United States Patent
Binch et al.

(10) Patent No.: US 8,076,343 B2
(45) Date of Patent: Dec. 13, 2011

(54) BENZIMIDAZOLES USEFUL AS INHIBITORS OF PROTEIN KINASES

(75) Inventors: Hayley Binch, San Diego, CA (US); Simon Everitt, Beaconsfield (GB); Michael Mortimore, Burford (GB); Daniel Robinson, Abingdon (GB); Dean Stamos, Carlsbad, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 70 days.

(21) Appl. No.: 11/492,643

(22) Filed: Jul. 21, 2006

(65) Prior Publication Data
US 2007/0099920 A1    May 3, 2007

Related U.S. Application Data

(60) Provisional application No. 60/702,399, filed on Jul. 26, 2005.

(51) Int. Cl.
*C07D 239/42*    (2006.01)
*C07D 401/04*    (2006.01)

(52) U.S. Cl. ......... 514/256; 514/275; 544/328; 544/331
(58) Field of Classification Search .................. None
See application file for complete search history.

(56) References Cited

FOREIGN PATENT DOCUMENTS
WO    WO 2004056786    *    7/2004
WO    WO 2005066156    *    7/2005

OTHER PUBLICATIONS

Dorwald, F.Z. Side Reactions in Organic Synthesis, 2005, p. IX of preface.*
Lyman et al. Blood, 1998, 91, 1101-34.*

* cited by examiner

*Primary Examiner* — Noble Jarrell
(74) *Attorney, Agent, or Firm* — H. Joon Chung

(57) ABSTRACT

The present invention relates to compounds useful as inhibitors of Aurora, FLT-3, or PDK1 protein kinase. The invention also provides pharmaceutically acceptable compositions comprising said compounds and methods of using the compositions in the treatment of various disease, conditions, or disorders. The invention also provides processes for preparing compounds of the invention.

20 Claims, No Drawings

BENZIMIDAZOLES USEFUL AS INHIBITORS OF PROTEIN KINASES

CROSS REFERENCE TO RELATED APPLICATIONS

This present application claims the benefit, under 35 U.S.C. §119, to U.S. Provisional Application No. 60/702,399 filed Jul. 26, 2005; the entire disclosure of which is incorporated herein by reference.

TECHNICAL FIELD OF THE INVENTION

This invention relates to compounds that are protein kinase inhibitors, compositions containing such compounds, processes for making such compounds, and methods of use. More particularly, the compounds are inhibitors of FLT-3, PDK1, and Aurora kinases and are useful for treating disease states, such as cancer, that are alleviated by these kinase inhibitors.

BACKGROUND OF THE INVENTION

The Aurora proteins are a family of three highly related serine/threonine kinases (termed Aurora-A, -B and -C) that are essential for progression through the mitotic phase of cell cycle. Specifically Aurora-A plays a crucial role in centrosome maturation and segregation, formation of the mitotic spindle and faithful segregation of chromosomes. Aurora-B is a chromosomal passenger protein that plays a central role in regulating the alignment of chromosomes on the meta-phase plate, the spindle assembly checkpoint and for the correct completion of cytokinesis.

Overexpression of Aurora-A, -B or -C has been observed in a range of human cancers including colorectal, ovarian, gastric and invasive duct adenocarcinomas.

A number of studies have now demonstrated that depletion or inhibition of Aurora-A or -B in human cancer cell lines by siRNA, dominant negative or neutralizing antibodies disrupts progression through mitosis with accumulation of cells with 4N DNA, and in some cases this is followed by endoreduplication and cell death.

FLT-3 plays an important role in the maintenance, growth and development of hematopoietic and non-hematopoietic cells. [Scheijen, B, Griffin J D, *Oncogene*, 2002, 21, 3314-3333 and Reilly, J T, *British Journal of Hematology*, 2002, 116, 744-757]. FLT-3 is a receptor tyrosine kinase which regulates the maintenance of stem cell/early progenitor pools as well the development of mature lymphoid and myeloid cells [Lyman, S, Jacobsen, S, *Blood*, 1998, 91, 1101-1134].

FLT-3 has been shown to play a role in a variety of hematopoietic and non-hematopoietic malignancies. Mutations that induce ligand independent activation of FLT-3 have been implicated in acute-myelogenous leukemia (AML), acute lymphocytic leukemia (ALL), mastocytosis and gastrointestinal stromal tumor (GIST). In addition to activating mutations, ligand dependent (autocrine or paracrine) stimulation of over-expressed wild-type FLT-3 can contribute to the malignant phenotype [Scheijen, B, Griffin J D, *Oncogene*, 2002, 21, 3314-3333].

PDK1 (the 3-phosphoinositide-dependent protein kinase-1) plays a key role in mediating many diverse cellular events by phosphorylating key regulatory proteins that play important roles controlling processes such as cell survival, growth, proliferation and glucose regulation [(Lawlor, M. A. et al., *J. Cell Sci.*, 114, pp. 2903-2910, 2001), (Lawlor, M. A. et al., *EMBO J.*, 21, pp. 3728-3738, 2002)]. Many human cancers including prostate and NSCL have elevated PDK1 signaling pathway function resulting from a number of distinct genetic events such as PTEN mutations or over-expression of certain key regulatory proteins [(Graff, J. R., *Expert Opin. Ther. Targets*, 6, pp. 103-113, 2002), (Brognard, J., et al., *Cancer Res.*, 61, pp. 3986-3997, 2001)]. Inhibition of PDK1 as a mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.*, 10, pp. 1439-1442, 2000).

Protein kinases are attractive and proven targets for new therapeutic agents to treat a range of human diseases, with examples including Gleevec and Tarceva. The Aurora, FLT-3, and PDK1 kinases are especially attractive due to their association with numerous human cancers and the roles they play in the proliferation of these cancer cells. Therefore, there is a need for compounds that inhibit protein kinases.

SUMMARY OF THE INVENTION

This invention provides compounds and pharmaceutically acceptable compositions thereof that are useful as inhibitors of protein kinases, such as Aurora protein kinases (Aurora A, Aurora B, Aurora C), FLT-3 kinase, and PDK1 kinase. These compounds have formula I:

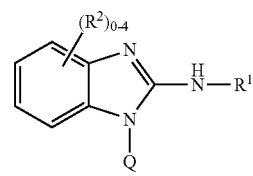

or a pharmaceutically acceptable salt thereof, wherein Q, $R^1$, and $R^2$ are as defined below.

These compounds and pharmaceutically acceptable compositions thereof are useful for treating or preventing a variety of diseases, disorders or conditions, including, but not limited to, cancer and other proliferative disorders.

The compounds provided by this invention are also useful for the study of kinases in biological and pathological phenomena; the study of intracellular signal transduction pathways mediated by such kinases; and the comparative evaluation of new kinase inhibitors.

This invention also provides processes for making the compounds of this invention.

DETAILED DESCRIPTION OF THE INVENTION

The present invention relates to a compound of formula I:

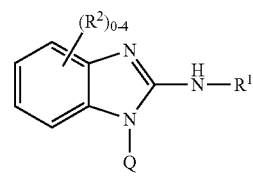

or a pharmaceutically acceptable salt thereof, wherein
Q is selected from the group consisting of

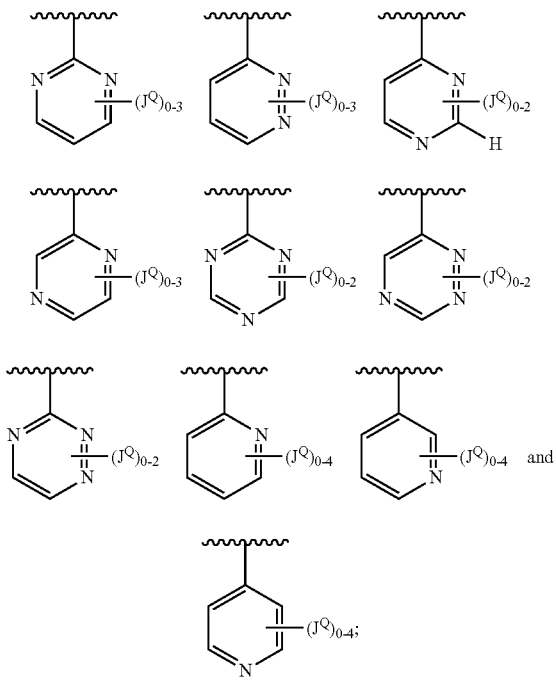

$R^1$ is H, $C_{1-6}$aliphatic, or $C_{3-8}$cycloaliphatic optionally substituted with 0-4 $J^R$;

each $R^2$ is independently $Z^R$, $M^R$, $(L^R)$-$Z^R$ or $(X^R)$-$M^R$;

each $J^Q$ is independently $Z^Q$, $M^Q$, $(L^Q)$-$Z^Q$, or $(X^Q)$-$M^Q$;

each $L^R$, $L^Q$, $X^R$, and $X^Q$ is independently $C_{1-6}$alkyl optionally interrupted with up to 2 occurrences of —NR—, —O—, —S—, —$CO_2$—, —OC(O)—, —C(O)CO—, —C(O)—, —C(O)NR—, —C(=N—CN), —C(=N—OH), —NRCO—, —NRC(O)O—, —$SO_2$NR—, —$NRSO_2$—, —NRC(O)NR—, —OC(O)NR—, —$NRSO_2$NR—, —SO—, or —$SO_2$—;
  wherein
  each $L^R$ is independently and optionally substituted with 0-2 $J^{LR}$;
  each $L^Q$ is independently and optionally substituted with 0-2 $J^{LQ}$;
  each $X^R$ is independently and optionally substituted with 0-2 $J^{XR}$;
  each $X^Q$ is independently and optionally substituted with 0-2 $J^{XQ}$;

each $Z^R$ and $Z^Q$ is independently H; $C_{1-6}$ aliphatic; a 3-8-membered saturated, partially unsaturated, or fully unsaturated monocyclic ring having 0-3 heteroatoms independently selected from nitrogen, oxygen, and sulfur; or an 8-12 membered saturated, partially unsaturated, or fully unsaturated bicyclic ring system having 0-5 heteroatoms independently selected from nitrogen, oxygen, and sulfur;
  wherein
  each $Z^R$ is independently and optionally substituted with 0-4 $J^{ZR}$;
  each $Z^Q$ is independently and optionally substituted with 0-4 $J^{ZQ}$;

each $M^R$ and $M^Q$ is independently halo, CN, $CF_3$, $NO_2$, OR, SR, or $N(R)_2$;

each $J^R$ is independently $C_{1-6}$aliphatic, $C_{1-6}$haloalkyl, halo, OH, $C_{1-3}$alkoxy, $NO_2$, or CN;

each $J^{LR}$, $J^{LQ}$, $J^{XR}$, $J^{XQ}$, $J^{ZR}$, and $J^{ZQ}$ is independently V, M, $(L^V)$—V, $(L^M)$-M, $C_{1-6}$haloalkyl, halo, OH, $C_{1-3}$alkoxy, $NO_2$, or CN;

each R is independently H, $C_{1-6}$aliphatic, $C_{6-10}$aryl, -($C_{1-6}$aliphatic)-($C_{6-10}$aryl), $C_{3-8}$cycloaliphatic, —C(=O)($C_{1-6}$aliphatic), —C(=O)($C_{3-8}$cycloaliphatic), or —C(=O)O($C_{1-6}$aliphatic); wherein each R is independently and optionally substituted with 0-2 J;

each $L^V$ and $L^M$ is independently $C_{1-6}$alkyl optionally interrupted with up to 2 occurrences of —NR—, —O—, —S—, —$CO_2$—, —OC(O)—, —C(O)CO—, —C(O)—, —C(O)NR—, —C(=N—CN), —C(=N—OH), —NRCO—, —NRC(O)O—, —$SO_2$NR—, —$NRSO_2$—, —NRC(O)NR—, —OC(O)NR—, —$NRSO_2$NR—, —SO—, or —$SO_2$—;
  wherein
  each $L^V$ is independently and optionally substituted with 0-2 $J^{LV}$;
  each $L^M$ is independently and optionally substituted with 0-2 $J^{LM}$;

each V is independently H; $C_{1-6}$ aliphatic; a 3-8-membered saturated, partially unsaturated, or fully unsaturated monocyclic ring having 0-3 heteroatoms independently selected from nitrogen, oxygen, and sulfur; or an 8-12 membered saturated, partially unsaturated, or fully unsaturated bicyclic ring system having 0-5 heteroatoms independently selected from nitrogen, oxygen, and sulfur; wherein each V is independently and optionally substituted with 0-2 $J^V$;

each J, $J^{LV}$, $J^{LM}$, and $J^V$ is independently R', $C_{3-6}$cycloalkyl, $C_{1-6}$haloalkyl, halo, $NO_2$, CN, OH, OR', SH, SR', $NH_2$, NHR', $N(R')_2$, COH, COR', $CONH_2$, CONHR', $CON(R')_2$, NHCOR', NR'COR', $NHCONH_2$, NHCONHR', NHCON$(R')_2$, NR'$CONH_2$, NR'CONHR', NR'$CON(R')_2$, $SO_2NH_2$, $SO_2$NHR', $SO_2N(R')_2$, $NHSO_2$R', or NR'$SO_2$R';

R' is unsubstituted $C_{1-6}$aliphatic; or two R' groups, together with the atom to which they are bound, form an unsubstituted 3-8 membered saturated or partially saturated monocyclic ring having 0-1 heteroatoms independently selected from nitrogen, oxygen, and sulfur;

each M is independently halo, CN, $CF_3$, $NO_2$, OH, O($C_{1-6}$alkyl), SH, S($C_{1-6}$alkyl), $NH_2$, NH($C_{1-6}$alkyl), or $N(C_{1-6}alkyl)_2$.

One embodiment provides that
when Q is

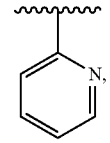

$R^2$ is not

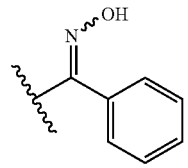

at the 5 or 6 position of the benzimidazole ring;

when Q is

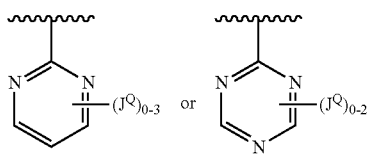

and $R^2$ is H, F, Cl, $CH_3$, $CF_3$, $OCH_3$, or $OCH_2CH_3$ at the 5 or 6 position of the benzimidazole ring, then $J^Q$ is not —O—($C_{1-3}$aliphatic);
when Q is

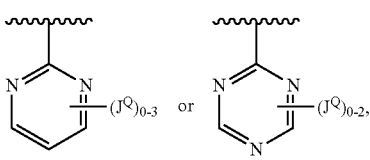

then $J^Q$ is not

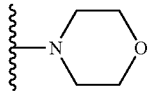

optionally substituted with methyl;
when $R^1$ and $R^2$ are H, then Q is not

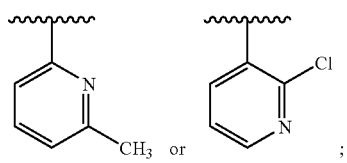

when Q is

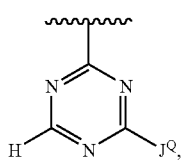

then $J^Q$ is not Cl, $NH_2$,

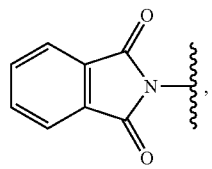

or NR"—Ar wherein
Ar is an optionally substituted group selected from phenyl, piperonyl, or pyridyl; and
R" is H or optionally substituted $C_{1-6}$aliphatic.

Compounds of this invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, Numbering for the benzimidazole ring is as shown below.

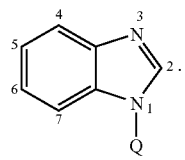

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups.

Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl. In some embodiments, said cycloaliphatic group can be "bridged".

A "bridged" ring consists of a ring containing an additional alkyl chain, wherein each end of said chain is bonded to a ring member of the ring, provided that both ends of the chain are not bonded to the same ring member. Said alkyl chain can be optionally interrupted with a heteroatom selected from O, N, and S. Examples of bridged cycloaliphatic groups include, but are not limited to, bicyclo[3.3.2]decane, bicyclo[3.1.1]heptane, and bicyclo[3.2.2]nonane.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members. In some embodiments, said ring is bridged. Examples of bridged heterocycles include, but are not limited to, 7-aza-bicyclo[2.2.1]heptane and 3-aza-bicyclo[3.2.2]nonane.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —R°; —OR°; —SR°; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; a 5-6 membered heteroaryl or heterocyclic ring optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; —P(O)$_2$R°; —PO(R°)$_2$; —OPO(R°)$_2$; or —(CH$_2$)$_{0-2}$NHC(O)R°; wherein each independent occurrence of R° is selected from hydrogen, optionally substituted $C_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R°, on the same substituent or different substituents, taken together with the atom(s) to which each R° group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of R° are selected from $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2(C_{1-4}aliphatic)$, $O(haloC_{1-4}\ aliphatic)$, or $haloC_{1-4}aliphatic$, wherein each of the foregoing $C_{1-4}$aliphatic groups of R° is unsubstituted.

An aliphatic group or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: $=O$, $=S$, $=NNHR^*$, $=NN(R^*)_2$, $=NNHC(O)R^*$, $=NNHCO_2(alkyl)$, $=NNHSO_2(alkyl)$, or $=NR^*$, where each $R^*$ is independently selected from hydrogen or an optionally substituted $C_{1-6}$ aliphatic group.

Unless otherwise defined above and herein, optional substituents on the nitrogen of a non-aromatic heterocyclic ring are generally selected from $-R^+$, $-N(R^+)_2$, $-C(O)R^+$, $-CO_2R^+$, $-C(O)C(O)R^+$, $-C(O)CH_2C(O)R^+$, $-SO_2R^+$, $-SO_2N(R^+)_2$, $-C(=S)N(R^{+1})_2$, $-C(=NH)-N(R^+)_2$, or $-NR^+SO_2R^+$; wherein $R^+$ is hydrogen, an optionally substituted $C_{1-6}$ aliphatic, optionally substituted phenyl, optionally substituted $-O(Ph)$, optionally substituted $-CH_2(Ph)$, optionally substituted $-(CH_2)_{1-2}(Ph)$; optionally substituted $-CH=CH(Ph)$; or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of $R^+$ are selected from $-NH_2$, $-NH(C_{1-4}\ aliphatic)$, $-N(C_{1-4}\ aliphatic)_2$, halogen, $C_{1-4}\ aliphatic$, $-OH$, $-O(C_{1-4}\ aliphatic)$, $-NO_2$, $-CN$, $-CO_2H$, $-CO_2(C_{1-4}\ aliphatic)$, $-O(halo\ C_{1-4}\ aliphatic)$, or $halo(C_{1-4}\ aliphatic)$, wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As detailed above, in some embodiments, two independent occurrences of R° (or $R^+$, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of R° (or $R^+$, R, R' or any other variable similarly defined herein), are taken together with the atom(s) to which each variable is bound include, but are not limited to, the following: a) two independent occurrences of R° (or $R^+$, R, R' or any other variable similarly defined herein) that are bound to the same atom and are taken together with that atom to form a ring, for example, $N(R°)_2$, where both occurrences of R° are taken together with the nitrogen atom to form a piperidin-1-yl, piperazin-1-yl, or morpholin-4-yl group; and b) two independent occurrences of R° (or $R^+$, R, R' or any other variable similarly defined herein) that are bound to different atoms and are taken together with both of those atoms to form a ring, for example where a phenyl group is substituted with two occurrences of OR°

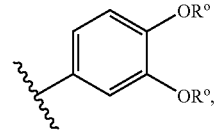

these two occurrences of R° are taken together with the oxygen atoms to which they are bound to form a fused 6-membered oxygen containing ring:

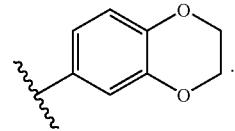

It will be appreciated that a variety of other rings can be formed when two independent occurrences of R° (or $R^+$, R, R' or any other variable similarly defined herein) are taken together with the atom(s) to which each variable is bound and that the examples detailed above and herein are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups include, but are not limited to, $-NR-$, $-O-$, $-S-$, $-CO_2-$, $-OC(O)-$, $-C(O)CO-$, $-C(O)-$, $-C(O)NR-$, $-C(=N-CN)$, $-NRCO-$, $-NRC(O)O-$, $-SO_2NR-$, $-NRSO_2-$, $-NRC(O)NR-$, $-OC(O)NR-$, $-NRSO_2NR-$, $-SO-$, or $-SO_2-$, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH₂CH₂CH₃ were optionally interrupted with —O—, the resulting compound could be —OCH₂CH₃, —CH₂OCH₃, or —CH₂CH₂OH.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Unless otherwise stated, a substituent can freely rotate around any rotatable bonds. For example, a substituent drawn as

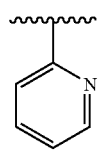

also represents

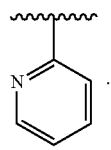

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

The following abbreviations are used:
DBU is diazabicycloundecane
DCM is dichloromethane
DIPEA is diisopropylethylamine
DMSO is dimethyl sulfoxide
DMF is dimethylformamide
EtOAc is ethyl acetate
HPLC is high performance liquid chromatography
i-PrOH is isopropyl alcohol
MeCN is acetonitrile
TEA is Triethylamine
TFA is trifluoroacetic acid
TMP is 2,2,6,6,tetramethylpiperidine
Rt is retention time
LCMS liquid chromatography mass spectrometry
$^1H$ NMR is nuclear magnetic resonance According to one embodiment of the invention, $R^1$ is H. In another embodiment, Q is

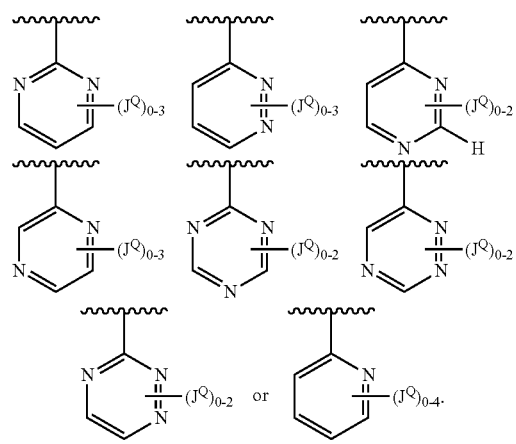

In some embodiments, Q is

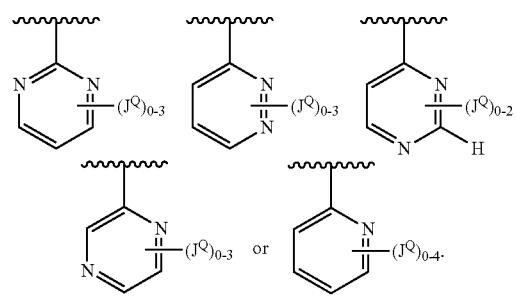

In some embodiments, Q is

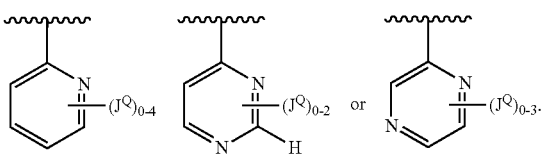

In other embodiments, Q is

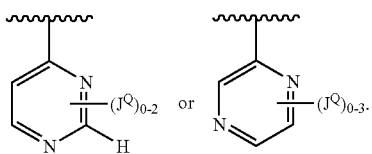

In yet other embodiments, Q is

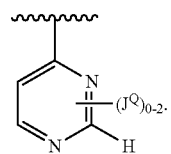

In some embodiments, $J^Q$ is $(L^Q)$-$Z^Q$ or $(X^Q)$-$M^Q$.

In some embodiments of this invention, Q is mono-substituted with $J^Q$ as shown in formula II

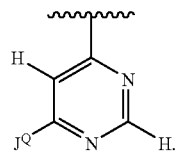

II

In some embodiments, $J^Q$ is $(L^Q)$-$Z^Q$.

In certain embodiments, $L^Q$ $C_{1-6}$alkyl optionally interrupted with up to 2 occurrences of —NR—, —O—, —S—, —C(O)—, —C(O)NR—, —NRCO—, —SO$_2$NR—, or —NRSO$_2$—.

In other embodiments, $L^Q$ is $C_{1-6}$alkyl optionally interrupted with up to 2 occurrences of —NR—, —O—, or —S—.

In some embodiments, $L^Q$ is $C_{1-6}$alkyl optionally interrupted with up to 1 occurrence of —NR—. In certain embodiments, the 1 occurrence of —NR— is attached directly to ring Q.

In some embodiments, $L^Q$ is —NH—, —NR—, —NH($C_{1-5}$alkyl)-, or —NR($C_{1-5}$alkyl)-; wherein R is $C_{1-6}$alkyl.

In some embodiments of this invention, each $J^{LQ}$ is independently halo, $C_{1-6}$aliphatic, or $C_{1-6}$haloalkyl.

In another embodiment of this invention, $Z^Q$ is selected from H or an optionally substituted group selected from $C_{1-6}$ aliphatic, $C_{3-10}$ cycloaliphatic, phenyl, 5-8 membered heteroaryl, and 5-8 membered heterocyclyl.

In some embodiments, $Z^Q$ is H or optionally substituted $C_{1-6}$ aliphatic.

In other embodiments, $Z^Q$ is optionally substituted phenyl.

In yet other embodiments, $Z^Q$ is a 5-8 membered heterocyclyl containing up to 2 heteroatoms selected from the group consisting of O, N, and S. In some embodiments, $Z^Q$ is a 5-8 membered heterocyclyl containing up 2 nitrogen atoms. In some embodiments, said heterocyclyl is piperidine, piperazine, homopiperidine, or homopiperazine. In some embodiments, said heterocyclyl is piperidine or piperazine.

In another embodiment of this invention, $J^Q$ is $(X^Q)$-$M^Q$.

In some embodiments, $X^Q$ is $C_{1-6}$alkyl optionally interrupted with up to 2 occurrences of —NR—, —O—, —S—, —C(O)—, —C(O)NR—, —NRCO—, —SO$_2$NR—, or —NRSO$_2$—. In some embodiments, $X^Q$ is $C_{1-6}$alkyl optionally interrupted with up to 2 occurrences of —NR—, —O—, or —S—. In other embodiments, $X^Q$ is $C_{1-6}$alkyl optionally interrupted with up to 1 occurrence of —NR—. In yet other embodiments, the 1 occurrence of —NR— is bonded directly to ring Q.

In some embodiments of this invention, each $J^{XQ}$ is independently halo, $C_{1-6}$aliphatic, or $C_{1-6}$haloalkyl.

In certain embodiments, $M^Q$ is OR or N(R)$_2$. In other embodiments, $M^Q$ is NH$_2$.

In some embodiments, $J^Q$ is $Z^Q$ or $M^Q$. In some embodiments, $J^Q$ is $Z^Q$. In other embodiments, $J^Q$ is $M^Q$.

In some embodiments, $J^Q$ is an optionally substituted group selected from N(R)$_2$, —NR—($C_{1-3}$alkyl)-N(R)$_2$, or —NR-(5-8 membered heterocyclyl).

In one embodiment of this invention, $J^Q$ is NH$_2$, —NHCH$_2$CH$_2$NH$_2$, —NHCH($J^{XQ}$)CH$_2$NH$_2$, or

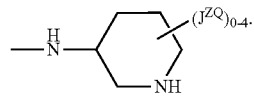

In some embodiments, $J^Q$ is —NHCH($J^{XQ}$)CH$_2$NH$_2$.

In some embodiments, $J^{XQ}$ is H, methyl, ethyl, propyl, isopropyl, butyl, isobutyl, sec-butyl, or tert-butyl.

In another embodiment, $R^2$ is selected from $Z^R$ or $M^R$.

In certain embodiments, $Z^R$ is H or an optionally substituted group selected from $C_{1-6}$ aliphatic, $C_{3-6}$cycloaliphatic, and $C_{3-6}$heterocyclyl. In some embodiments, $Z^R$ is H or optionally substituted $C_{1-6}$ aliphatic. In some embodiments, $Z^R$ is an optionally substituted group selected from $C_{1-6}$ aliphatic, $C_{3-6}$cycloaliphatic, and $C_{3-6}$heterocyclyl.

In some embodiments, $M^R$ is halo, CN, CF$_3$, NO$_2$, OR, or N(R)$_2$ wherein R is H or $C_{1-3}$alkyl.

One embodiment of this invention can be represented by Formula II-a:

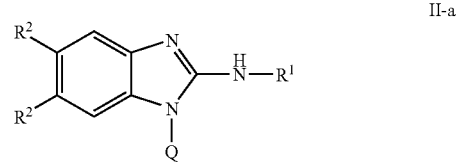

II-a

Another embodiment of this invention can be represented by Formula III:

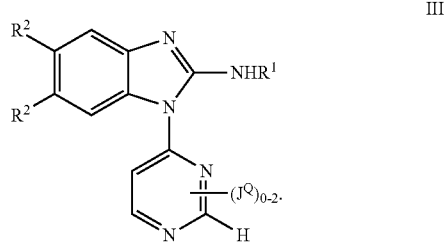

III

Another embodiment of this invention can be represented by Formula III-a:

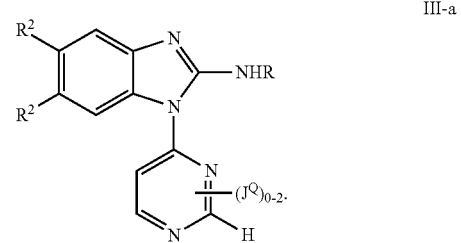

III-a

In some embodiments of this invention, at least one $R^2$ is not H. In some embodiments, neither $R^2$ is H. In some embodiments, each $R^2$ is independently $Z^R$ or $M^R$. In some embodiments, both $R^2$ groups are $Z^R$ or $M^R$. In some embodiments, both $R^2$ groups are $Z^R$. In other embodiments, $R^2$ is $C_{1-3}$alkyl. In some embodiments, $R^2$ is methyl.

In some embodiments, $Z^R$ is $C_{1-6}$ aliphatic; a 3-8-membered saturated, partially unsaturated, or fully unsaturated monocyclic ring having 0-3 heteroatoms independently selected from nitrogen, oxygen, and sulfur; or an 8-12 membered saturated, partially unsaturated, or fully unsaturated bicyclic ring system having 0-5 heteroatoms independently selected from nitrogen, oxygen, and sulphur. In some embodiments, $Z^R$ is $C_{1-6}$ aliphatic.

In some embodiments, the variables are as depicted in the compounds of Table 1.

Representative compounds of this invention are set forth below in Table 1.

TABLE 1

Examples of Compounds of Formula I

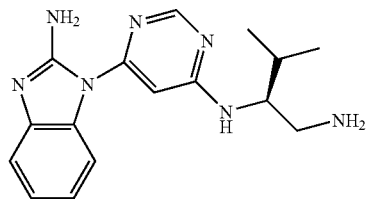

1

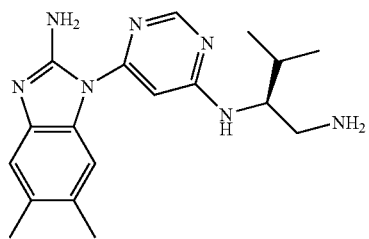

2

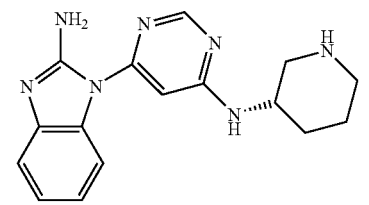

3

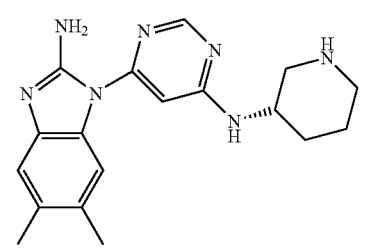

4

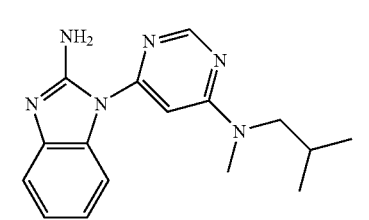

5

TABLE 1-continued

Examples of Compounds of Formula I

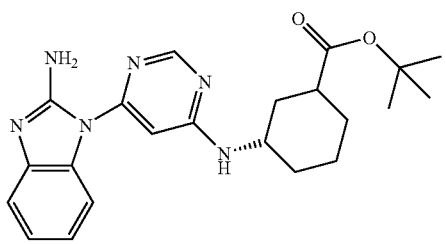

6

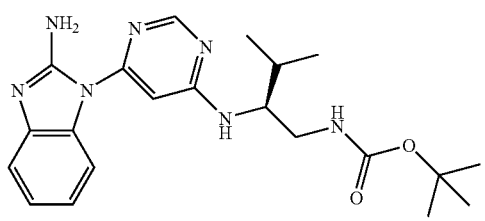

7

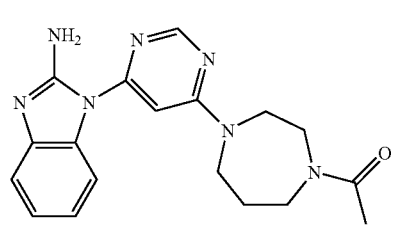

8

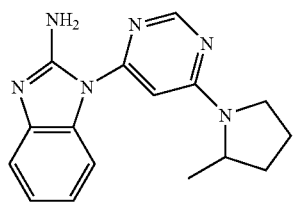

9

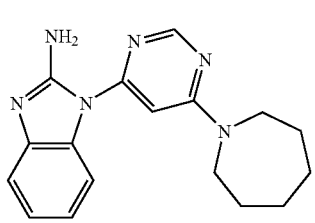

10

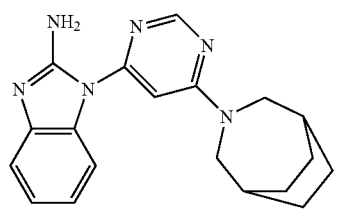

11

TABLE 1-continued
Examples of Compounds of Formula I
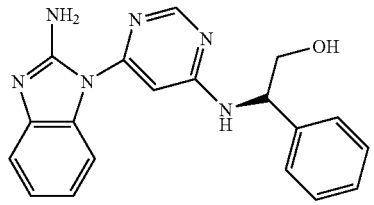
12
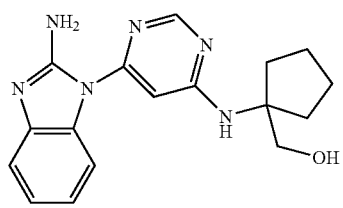
13
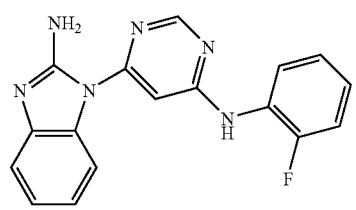
14
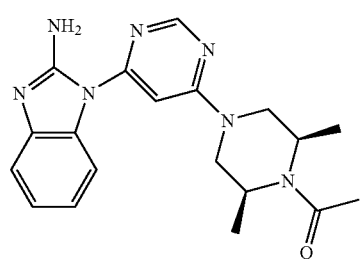
15
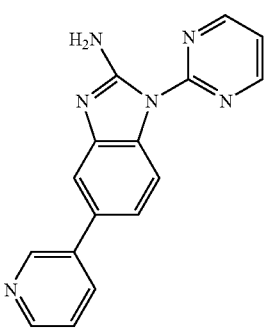
16
TABLE 1-continued
Examples of Compounds of Formula I
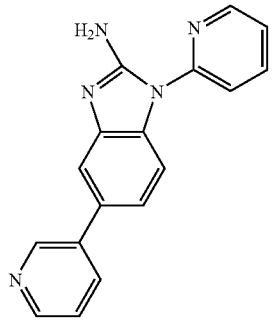
17
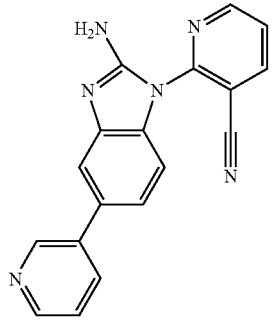
18
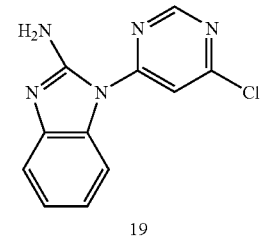
19
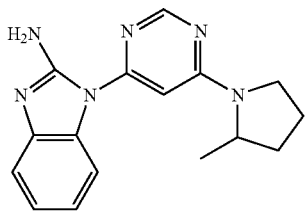
20
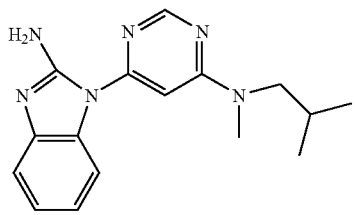
21

TABLE 1-continued
Examples of Compounds of Formula I
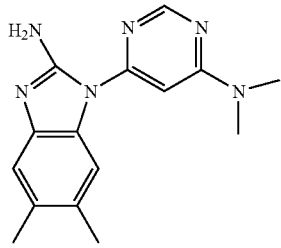
22
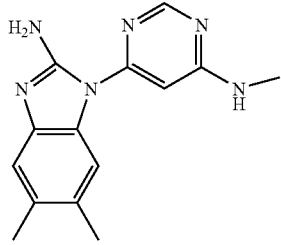
23
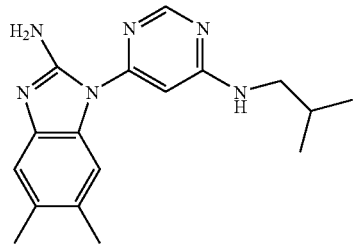
24
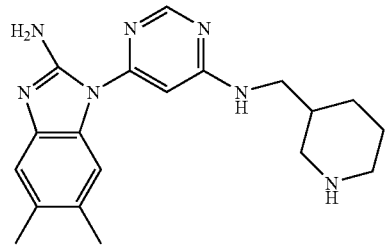
25
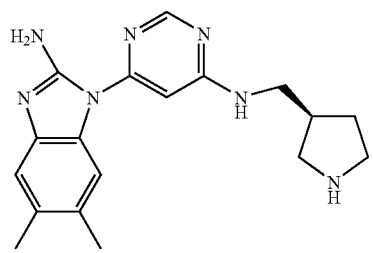
26
TABLE 1-continued
Examples of Compounds of Formula I
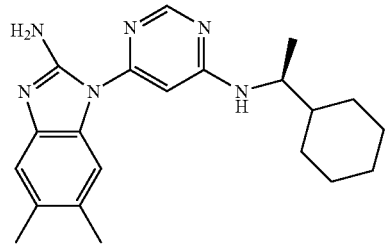
27
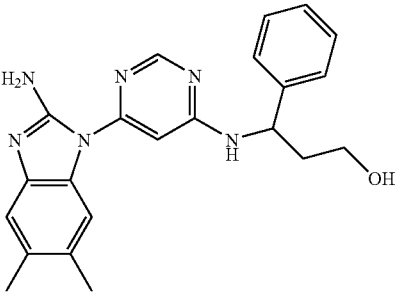
28
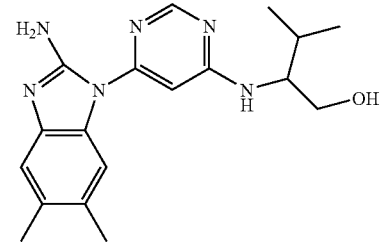
29
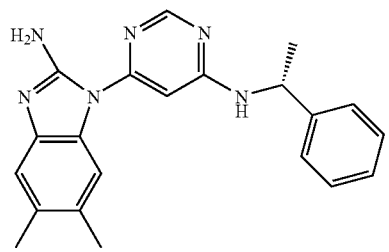
30
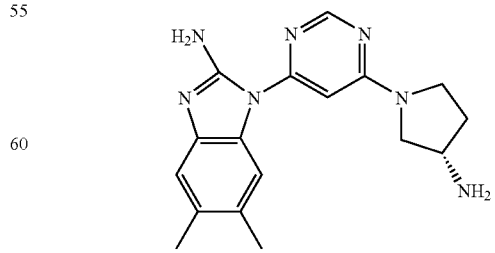
31

TABLE 1-continued
Examples of Compounds of Formula I
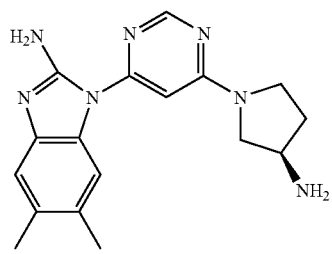
32
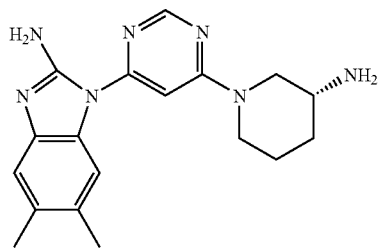
33
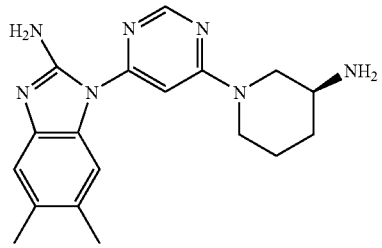
34
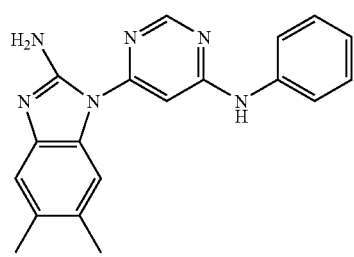
35
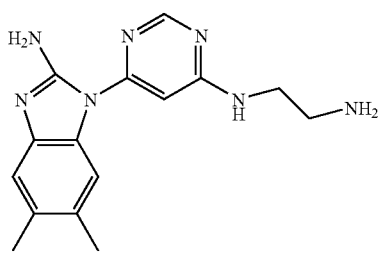
36
TABLE 1-continued
Examples of Compounds of Formula I
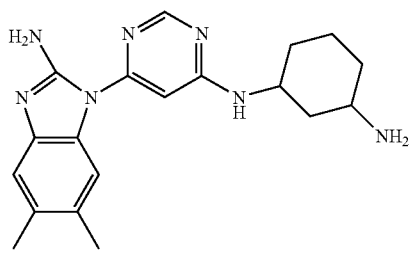
37
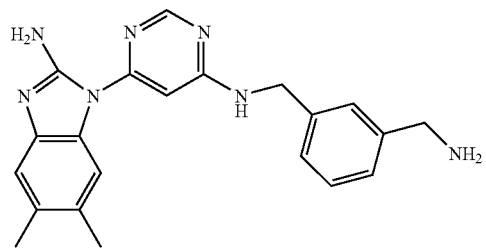
38
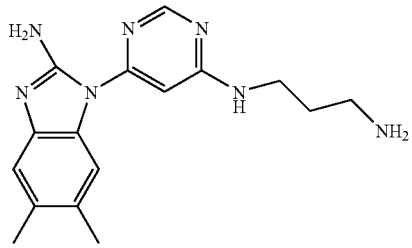
39
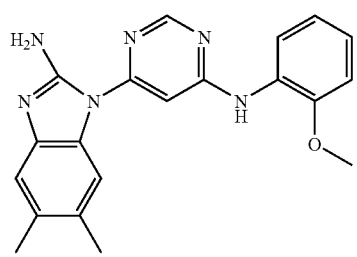
40
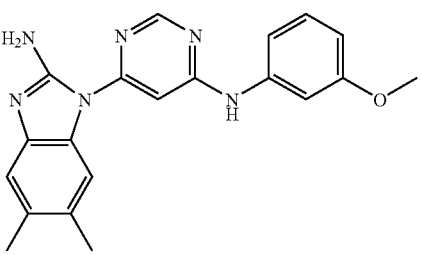
41

TABLE 1-continued
Examples of Compounds of Formula I
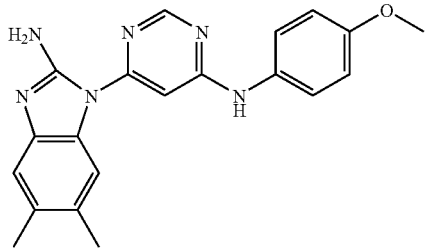
42
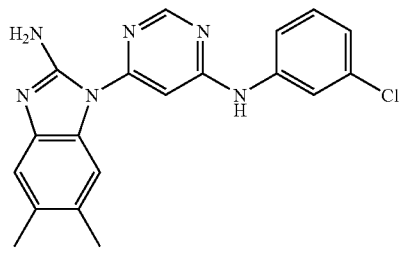
43
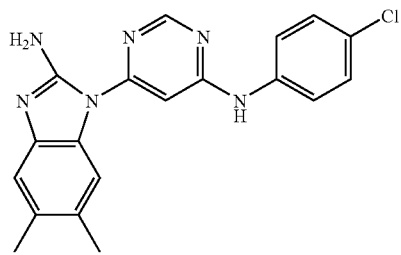
44
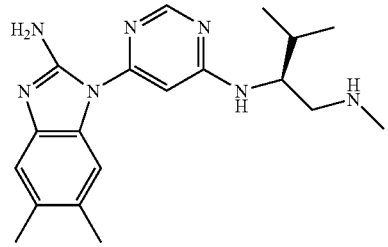
45
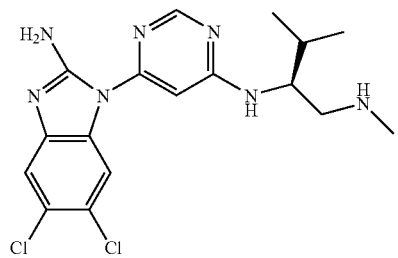
46
TABLE 1-continued
Examples of Compounds of Formula I
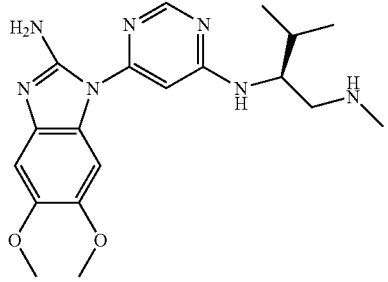
47
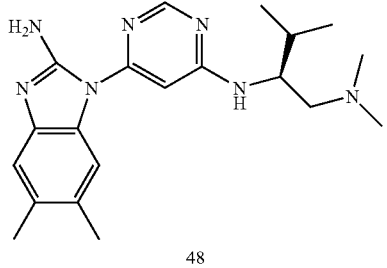
48
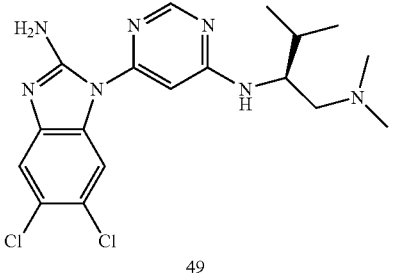
49
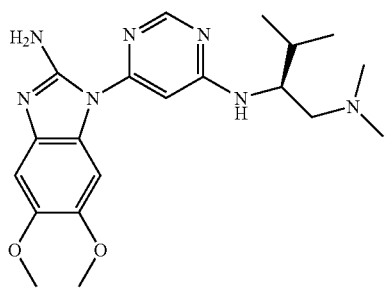
50
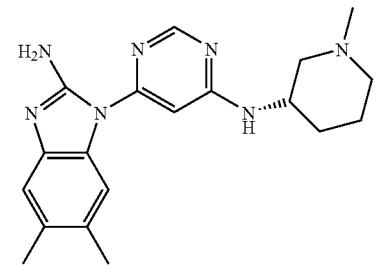
51

TABLE 1-continued

Examples of Compounds of Formula I

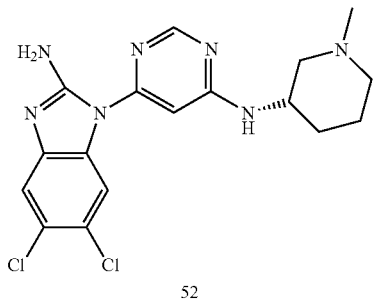
52

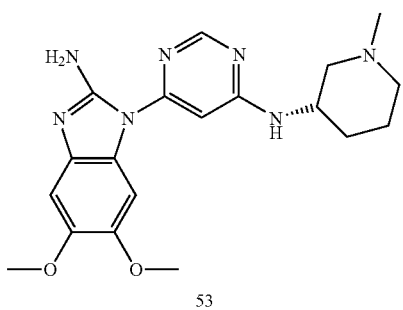
53

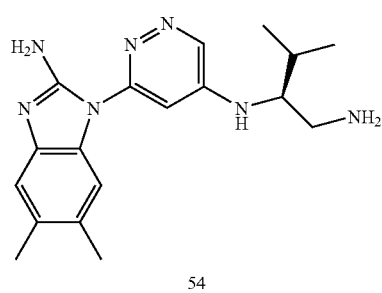
54

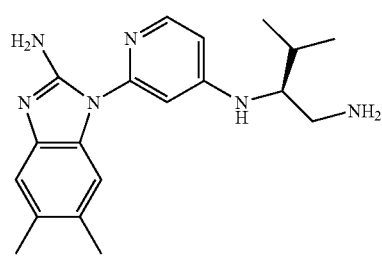
55

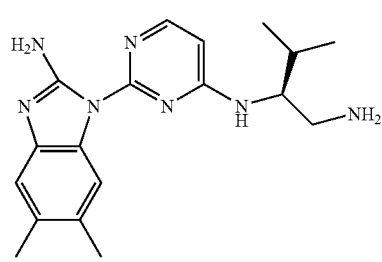
56

TABLE 1-continued

Examples of Compounds of Formula I

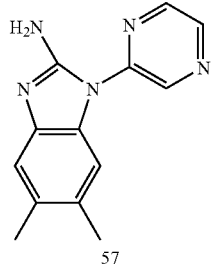
57

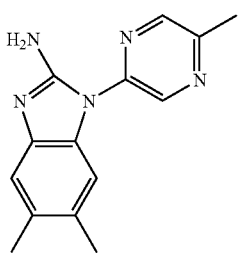
58

The compounds of this invention may be prepared in general by methods known to those skilled in the art for analogous compounds and as illustrated by the schemes below.

Scheme I

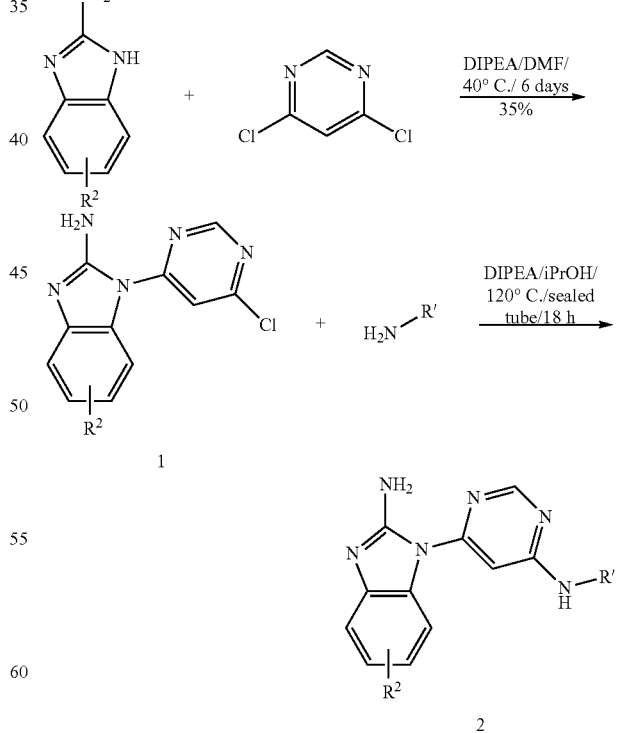

Scheme I depicts a method of making compounds wherein Q is 2,4-pyrimidine. NHR' represents $J^Q$ groups wherein $J^Q$ is attached to the pyrimidine via a nitrogen atom.

Scheme I′

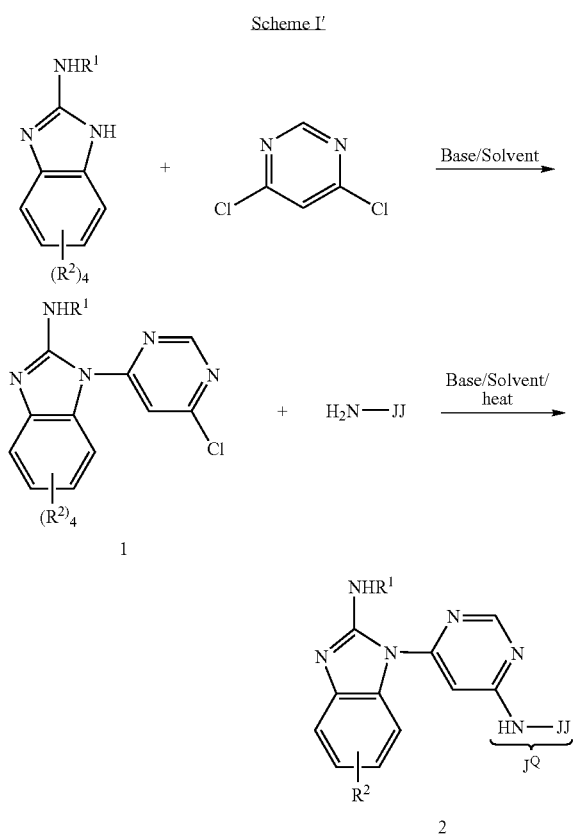

Scheme I′ depicts a method of making compounds wherein Q is 2,4-pyrimidine. NH-JJ represents $J^Q$ groups wherein $J^Q$ is attached to the pyrimidine via a nitrogen atom.

Scheme I-a

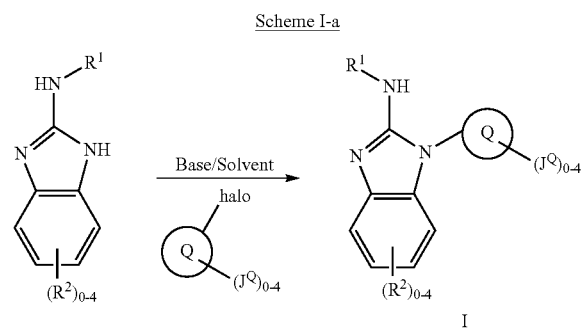

Scheme I-a depicts a method of making compounds wherein Q is

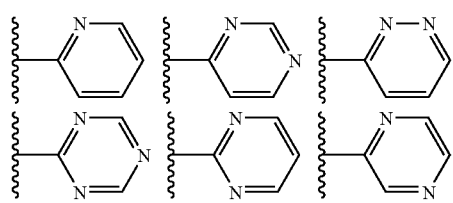

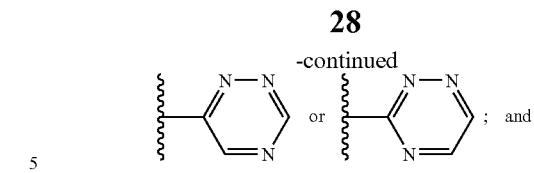

$R^1$, $R^2$, and $J^Q$ are as defined herein.

Examples of suitable bases that can be used in Scheme I-a include, but are not limited to, DIPEA, TEA, DBU, and TMP.

Examples of suitable solvents that can be used in Scheme I-a include, but are not limited to, DMF, i-PrOH, n-butanol, t-butanol, acetonitrile, THF, and dioxane.

Scheme I-b

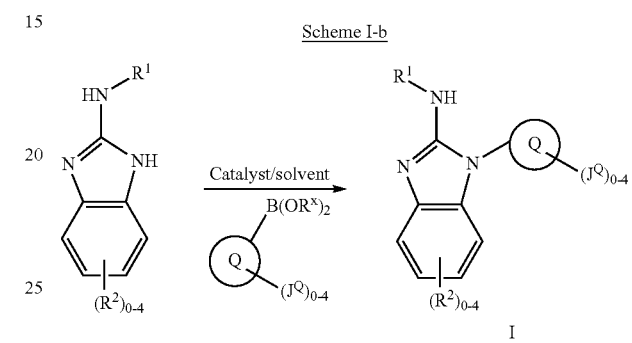

Scheme I-b depicts a method of making compounds wherein Q is

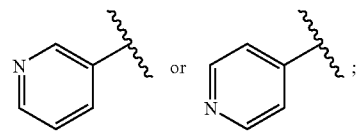

$R^1$, $R^2$, and $J^Q$ are as defined herein;

and $—B(OR^X)_2$ represents boronic esters or acids known to one skilled in the art.

As would be recognized by one of skill in the art, boronic acids and esters can be coupled to the nitrogen atom of a benzimidazole via a variety of known conditions. Typically, the conditions include, but are not limited to, a catalyst, a base, and a ligand in a suitable solvent.

Examples of suitable catalysts include, but are not limited to, $Pd(OAc)_2$ and $Pd_2(dba)_3$.

Examples of suitable solvents include, but are not limited to, toluene, xylene, and dioxane.

Examples of suitable bases include, but are not limited to, sodium tert-butoxide, potassium tert-butoxide, and $Cs_2CO_3$.

Examples of suitable ligands include, but are not limited to, BINAP, DPPF, (o-tol)3P, and (±) PPF-OMe.

Scheme II

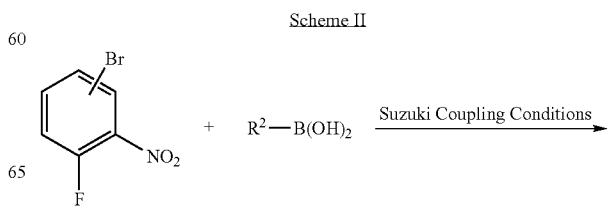

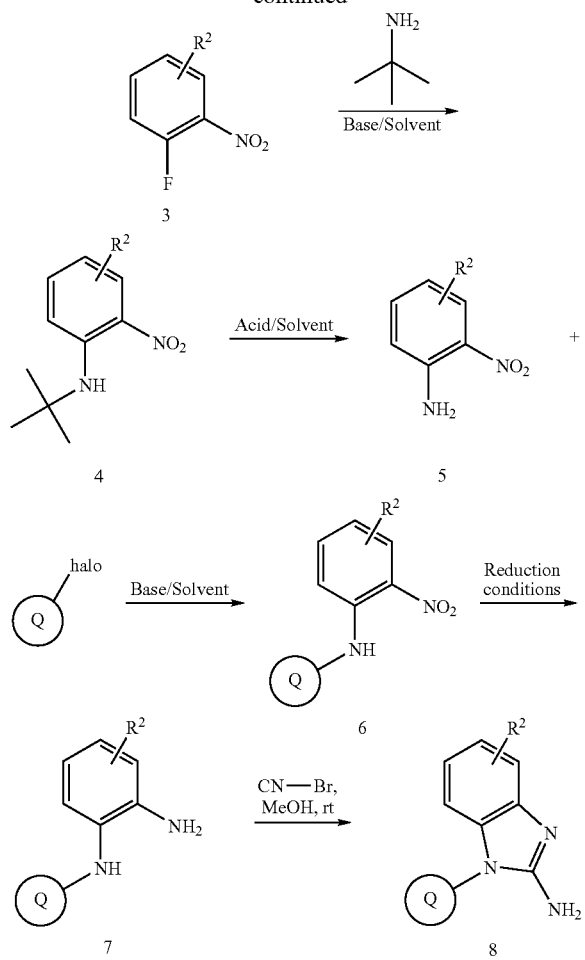

Scheme II depicts a method of making compounds wherein R² is aryl or heteroaryl.

One embodiment provides a process of preparing a compound of formula I:

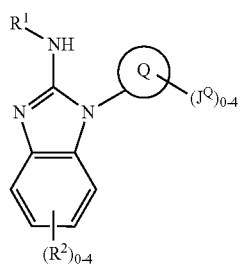
I wherein R¹, R², and $J^Q$ are as defined herein;
and Ring Q is

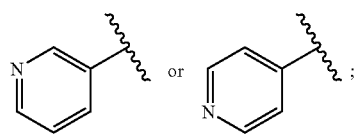

comprising reacting a compound of formula a:

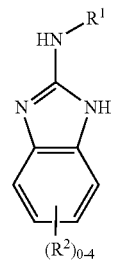
a wherein R¹ and R² are as defined herein;
with a compound of formula b:

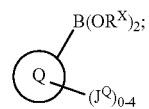
b wherein Ring Q is

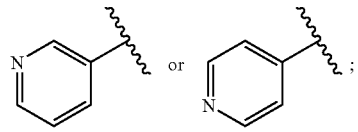

and $J^Q$ is as defined herein;
under suitable boronic acid/ester coupling conditions.

Another embodiment provides a process of preparing a compound of formula I:

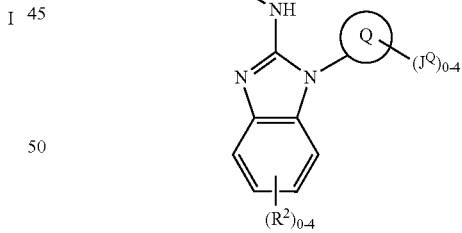
I wherein R¹, R², and $J^Q$ are as defined herein;
and Ring Q is

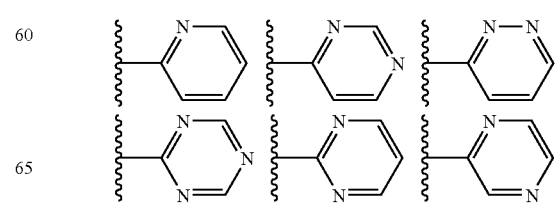

-continued

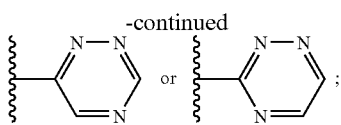

comprising reacting a compound of formula a:

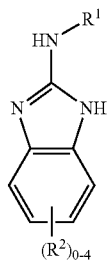

wherein $R^1$ and $R^2$ are as defined herein;
with a compound of formula c:

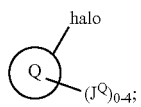

wherein $J^Q$ is as defined herein; and
Ring Q is

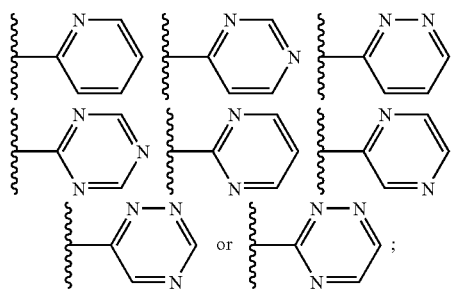

under suitable displacement conditions.

In some embodiments, halo in formula c is chloro.

Another embodiment provides a process of preparing a compound of formula I:

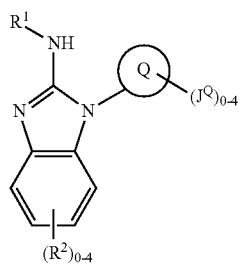

wherein $R^2$, $R^2$, Ring Q, and $J^Q$ are as defined herein;

comprising cyclizing a compound of formula 7:

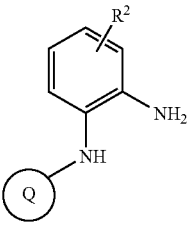

wherein $R^2$ and Ring Q are as defined herein;
with CN—Br under suitable cyclization conditions. Examples of cyclization conditions include, but are not limited to, stirring in MeOH at RT for 30 h.

Another embodiment provides a process of preparing a compound of formula 7 comprising reducing a compound of formula 6;

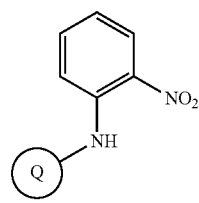

wherein $R^2$ and Ring Q are as defined herein;
under reduction conditions known to one skilled in the art to form a compound of formula 7. Examples of reduction conditions include, but are not limited to, $SnCl_2/EtOH$, Fe/AcOH, In/HCl, and Pd/C.

Another embodiment provides a process of preparing a compound of formula 6 comprising reacting a compound of formula 5;

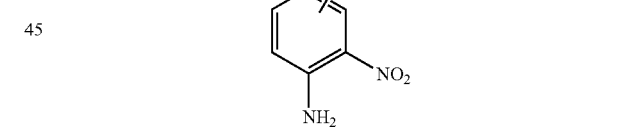

wherein $R^2$ is as defined herein; with

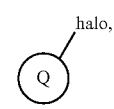

wherein Ring Q is as defined herein; under suitable displacement conditions to form a compound of formula 6. Suitable displacement conditions include, but are not limited to, a base and a solvent. Examples of suitable bases include, but are not limited to, $Cs_2CO_3$ and $K_2CO_3$. Suitable solvents include, but are not limited to, DMF and EtOH.

Another embodiment provides a process of preparing a compound of formula 5 comprising deprotecting a compound of formula 4;

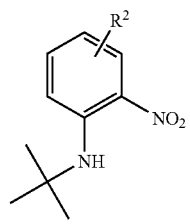

4 under suitable deprotection conditions known to one of skill in the art, to form a compound of formula 5. Examples of suitable deprotection conditions include, but are not limited to, the use of an acid (such as HCl or $H_2SO_4$) in a suitable solvent (such as MeOH, EtOH).

Another embodiment provides a process of preparing a compound of formula 4 comprising reacting a compound of formula 3:

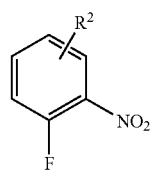

3 with $H_2N-C(CH_3)_3$ under suitable displacement conditions to form a compound of formula 4. Suitable displacement conditions include, but are not limited to, a suitable base, such as DIPEA, TEA, DBU, or TMP, in a suitable solvent, such DMF, dioxane, or THF.

Another embodiment provides a process of preparing a compound of formula 3 comprising coupling

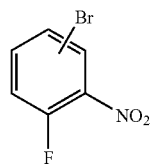

with $R^2-B(OR^X)_2$, wherein $R^2$ is as defined herein and $-B(OR^X)_2$ represents boronic esters or acids known to one skilled in the art; under suitable Suzuki (boronic acid/ester) coupling conditions known to one of skill in the art, to form a compound of formula 3. Suitable Suzuki coupling conditions typically involve the use of a catalyst, a base, and a boronic acid or ester in a suitable solvent. Examples of suitable catalysts include, but are not limited to, $Pd(PPh_3)_2Cl_2$, $Pd(PPh_3)_4$, and $PdCl_2(dppf)$. Suitable bases include, but are not limited to, $K_2CO_3$ and $Na_2CO_3$. Suitable solvents include, but are not limited to, tetrahydrofuran, dioxane, toluene, and ethanol.

Another embodiment provides a process of preparing a compound of formula 1:

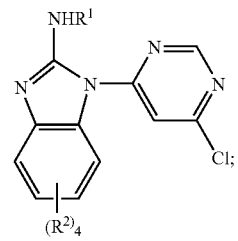

1 comprising reacting a compound of formula a:

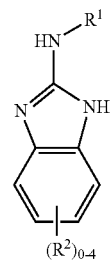

a wherein $R^1$ and $R^2$ are as defined herein; with

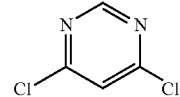

under suitable displacement conditions to form a compound of formula 1. Suitable displacement conditions include, but are not limited to, a suitable base, such as DIPEA, TEA, DBU, or TMP, in a suitable solvent, such DMF, dioxane, or THF.

Another embodiment provides a process of preparing a compound of formula 2:

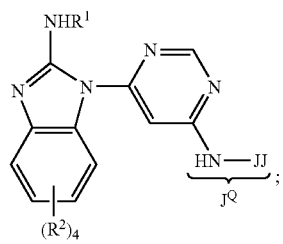

2 comprising heating the compound of formula 1 with $NH_2$-JJ (a $J^Q$ group that contains a reactive amino group), under suitable displacement conditions, to form the compound of formula 2. Suitable displacement conditions include, but are not limited to, heating a suitable base, such as DIPEA, TEA, DBU, or TMP, in a suitable solvent, such DMF, isopropanol, dioxane, or THF.

One aspect of this invention relates to a method for treating a disease state in patients that is alleviated by treatment with a protein kinase inhibitor, which method comprises administering to a patient in need of such a treatment a therapeutically effective amount of a compound of formula I.

The method is particularly useful for treating a disease state that is alleviated by the use of an inhibitor of the Aurora kinases (Aurora A, Aurora B, Aurora C), FLT-3, or PDK1.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from camptothecin, doxorubicin, idarubicin, Cisplatin, taxol, taxotere, vincristine, tarceva, the MEK inhibitor, U0126, a KSP inhibitor, or vorinostat.

The protein kinase inhibitors or pharmaceutical salts thereof may be formulated into pharmaceutical compositions for administration to animals or humans. These pharmaceutical compositions, which comprise an amount of the protein inhibitor effective to treat or prevent an Aurora, FLT-3, or PDK1 mediated condition and a pharmaceutically acceptable carrier, are another embodiment of the present invention.

The term "protein kinase-mediated condition", as used herein means any disease or other deleterious condition in which a protein kinase is known to play a role. Such conditions include, without limitation, autoimmune diseases, inflammatory diseases, neurological and neurodegenerative diseases, cancer, cardiovascular diseases, allergy and asthma.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions. In some embodiments, the cancer is selected from colorectal, thyroid, or breast cancer. The term "Aurora-mediated condition" or "Aurora-mediated disease" as used herein means any disease or other deleterious condition in which Aurora (Aurora A, Aurora B, and Aurora C) is known to play a role. Such conditions include, without limitation, cancer such as colorectal, thyroid, and breast cancer; and myeloproliferative disorders, such as polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

The term "FLT-3-mediated disease" or "FLT-3-mediated condition", as used herein means any disease or other deleterious condition in which a FLT-3 family kinase is known to play a role. Such conditions include, without limitation, hematopoietic disorders, in particular, acute-myelogenous leukemia (AML), chronic-myelogenous leukemia (CML), acute-promyelocytic leukemia (APL), and acute lymphocytic leukemia (ALL).

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

This invention also includes pharmaceutically acceptable salts of the compounds of this invention.

Pharmaceutically acceptable salts of the compounds of this invention include those derived from pharmaceutically acceptable inorganic and organic acids and bases. Examples of suitable acid salts include, but are not limited to, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include, but are not limited to, alkali metal (e.g., sodium and potassium), alkaline earth metal (e.g., magnesium), ammonium and $N^+(C_{1-4}\text{alkyl})_4$ salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include, but are not limited to, lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

One embodiment of this invention provides a method for treating or preventing an Aurora-mediated condition comprising the step of administering to a patient one of the compounds or pharmaceutical compositions described herein. The term "patient", as used herein, means an animal, preferably a human.

Another embodiment provides a method for treating or preventing a FLT-3-mediated condition comprising the step of administering to a patient a compound of formula I or a composition comprising said compound.

Yet another embodiment provides a method for treating or preventing a proliferative disorder or cancer comprising the step of administering to a patient a compound of formula I or a composition comprising said compound.

Another aspect of the invention relates to inhibiting Aurora or FLT-3 activity in a patient, which method comprises administering to the patient a compound of formula I or a composition comprising said compound.

One embodiment provides a method of inhibiting Aurora protein kinase activity in a patient comprising administering to a patient a compound of formula I or a composition comprising said compound.

Another embodiment provides a method of inhibiting FLT-3 protein kinase activity in a patient comprising administering to a patient a compound of formula I or a composition comprising said compound.

Yet another embodiment provides a method of inhibiting PDK1 protein kinase activity in a patient comprising administering to a patient a compound of formula I or a composition comprising said compound.

In some embodiments, these methods are used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, cystic fibrosis, and viral disease, or any specific disease or disorder described herein.

According to another embodiment, the invention provides methods for treating or preventing a condition selected from a proliferative disorder or cancer comprising the step of administering to a patient one of the compounds or pharmaceutical compositions described herein.

In some embodiments, the invention provides methods for treating or preventing cancer comprising the step of administering to a patient one of the compounds or pharmaceutical compositions described herein. In some embodiments, said cancer is selected from brain (gliomas), breast, colon, head and neck, kidney, lung, liver, melanoma, ovarian, pancreatic, prostate, sarcoma, or thyroid. In other embodiments, said cancer is selected from melanoma, myeloma, leukemia, lymphoma, neuroblastoma, or a cancer selected from colon, breast, gastric, ovarian, cervical, lung, central nervous system (CNS), renal, prostate, bladder, or pancreatic cancer. In yet other embodiments, said cancer is selected from pancreatic, prostate, or ovarian cancer.

According to another embodiment, the invention provides methods for treating or preventing a FLT-3-mediated condition comprising the step of administering to a patient a compound of formula I or a composition comprising said compound.

Preferably, that method is used to treat or prevent a condition selected from hematopoietic disorders, in particular, acute-myelogenous leukemia (AML), acute-promyelocytic leukemia (APL), chronic-myelogenous leukemia (CML), and acute lymphocytic leukemia (ALL).

Another aspect of the invention relates to inhibiting Aurora, FLT-3, or PDK1 activity in a patient, which method comprises administering to the patient a compound of formula I or a composition comprising said compound.

Another aspect of the invention relates to inhibiting Aurora, FLT-3, or PDK1 activity in a biological sample or a patient, which method comprises contacting said biological sample with a compound of formula I or a composition comprising said compound. The term "biological sample", as used herein, means an in vitro or an ex vivo sample, and includes, without limitation, cell cultures or extracts thereof; biopsied material obtained from a mammal or extracts thereof; and blood, saliva, urine, feces, semen, tears, or other body fluids or extracts thereof.

Inhibition of Aurora, FLT-3, or PDK1 activity in a biological sample is useful for a variety of purposes that are known to one of skill in the art. Examples of such purposes include, but are not limited to, blood transfusion, organ-transplantation, biological specimen storage, and biological assays.

Another embodiment provides a method of treating cancer in a patient in need thereof comprising the step of disrupting mitosis of the cancer cells by inhibiting Aurora with a compound of formula I or a composition comprising said compound.

Another embodiment provides a method of treating cancer in a patient in need thereof comprising the step of disrupting mitosis of the cancer cells by inhibiting FLT-3 with a compound of formula I or a composition comprising said compound.

Depending upon the particular diseases or conditions to be treated or prevented, additional drugs, which are normally administered to treat or prevent that condition, may be administered together with the inhibitors of this invention. For example, chemotherapeutic agents or other anti-proliferative agents may be combined with the Aurora, FLT-3, or PDK1 inhibitors of this invention to treat proliferative diseases.

Those additional agents may be administered separately, as part of a multiple dosage regimen, from the Aurora, FLT-3, or PDK1 inhibitor-containing compound or composition. Alternatively, those agents may be part of a single dosage form, mixed together with the Aurora, FLT-3, or PDK1 inhibitor in a single composition.

In order that this invention be more fully understood, the following preparative and testing examples are set forth. These examples are for the purpose of illustration only and are not to be construed as limiting the scope of the invention in any way.

Example 1

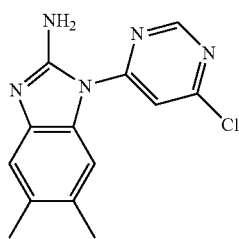

(1)

1-(6-chloropyrimidin-4-yl)-5,6-dimethyl-1H-benzo[d] imidazol-2-amine (1): A round bottom flask was charged with 4,6-dichloropyrimide (1.69 g, 11.3 mmol), 2-amino-5,6-dimethylbenzimidazole (1.83 g, 11.3 mmol), DIPEA (1.92 ml, 11.3 mmol) and DMF (50 ml). The reaction mixture was vigorously stirred at 80° C. for 6 days and then allowed to cool the room temperature. The volatile components of the reaction mixture were then removed in vacuo and the residue adsorbed onto silica and then purified by column chromatography using as eluent, hexanes (40-60)/EtOAc 0% to 100%, to afford a yellow solid (1.09 g, 35%). 1H NMR (CDCl$_3$): 2.35 (3H, s), 2.39 (3H, s), 6.43 (2H, brs), 7.25 (2H, m), 7.75 (1H, s), 8.93 (1H, s). LC/MS 374.30 [M+H] 372.50 [M−H].

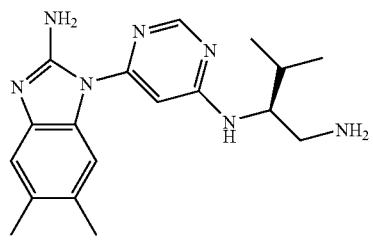

(2)

1-(6-((S)-1-amino-3-methylbutan-2-ylamino)pyrimidin-4-yl)-5,6-dimethyl-1H-benzo[d]imidazol-2-amine, diTFA salt (Compound 2): A tube was charged with 1-(6-chloropyrimidin-4-yl)-5,6-dimethyl-1H-benzo[d]imidazol-2-amine (1) (0.27 g, 1.0 mmol), tert-butyl (S)-2-amino-3-methylbutylcarbamate (0.20 g, 1.0 mmol), DIPEA (0.34 ml, 2.0 mmol) and isopropyl alcohol (5 ml) and then sealed and heated to 120° C. for 2 days. After cooling to room temperature, the volatile components were removed in vacuo and the residue purified by column chromatography using as eluent hexanes (40-60)/EtOAc 0% to 100%, to afford a waxy white solid. This material was dissolved in DCM (5 ml) and TFA (2 ml) and stirred at room temperature for 2 h. The volatile components were then removed in vacuo and the residue purified by preparative HPLC on a C-18 reverse phase column, using as eluent a 0% to 100% gradient of MeCN and water/0.05% w/v TFA. The fractions containing product we then freeze dried, affording the desired product as a white solid (0.13 g, 29.6%) 1H NMR (DMSO-d$_6$): 0.94 (6H, m), 1.95 (1H, m), 2.31 (6H, s), 2.87 (1H, m), 3.11 (1H, m), 4.34 (1H, s), 6.90 (1H, s), 7.25 (1H, s), 7.36 (1H, s), 7.94 (4H, m), 8.55 (1H, s), 8.84 (2H, s); LC/MS 340.45 [M+H] 338.63 [M−H].

Compounds 1-15 and 19-44 were made in a manner similar to Example 1. Compounds 45-58 can also be made in a manner similar to Example 1.

Example 2

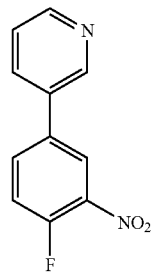

(3)

3-(4-fluoro-3-nitrophenyl)pyridine 2.0 g of 3-pyridine boronic acid, 3.22 g of 4-Bromo-1-fluoro-2-nitro benzene, and 285 mg of Pd (PPh$_3$)$_2$Cl$_2$ were sequentially added to 50 mL of degassed 1,4-dioxane and the mixture was stirred at rt for 20 min. 50 mL of degassed aqueous sodium carbonate solution (1M) was added and the reaction mixture was heated under argon at reflux for 1.5 h. The solvent was removed in vacuo, ethyl acetate was added, and the solution was filtered through celite. The filtrate was washed with brine, dried over MgSO$_4$ and concentrated to obtain crude compound 3 as dark brown color solid. The crude mixture was purified by column chromatography on a 60-120 mesh silica gel column using 2% MeOH/CHCl$_3$ as eluent to form a yellow solid (1.58 g, 80%). m.p. 87-88° C.;

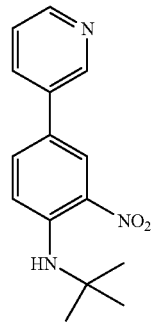

(4)

N-tert-butyl-2-nitro-4-(pyridin-3-yl)benzenamine To the stirred solution of 1.58 g of 3-(4-fluoro-3-nitrophenyl)pyridine in 5.0 mL DMF was added 1.124 g of N-ethyl diisopropylamine followed by 2.116 g of tert-butyl amine under nitrogen atmosphere. The reaction mixture was maintained at 50° C. for 5.0 h. The reaction mixture was diluted with ethyl acetate and water. Organic layer was separated and washed with water followed by brine solution. Organic layer was dried over sodium sulfate and evaporated to afford an orange solid (1.57 g, 85%) m.p. 67-69° C.;

(5)

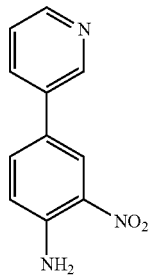

2-nitro-4-(pyridin-3-yl)benzenamine To a stirred solution of 1.5 g of N-tert-butyl-2-nitro-4-(pyridin-3-yl)benzenamine in 15 mL of methanol was added 9 mL of 6 N HCl. The solution was refluxed for 3 h. The reaction mass was then diluted with chloroform and pH was adjusted to 7 using sat. NaHCO₃ solution. The organic layer was separated, washed with water followed by brine, dried over sodium sulfate, and evaporated to afford an orange solid (1.06 g, 90%).

6

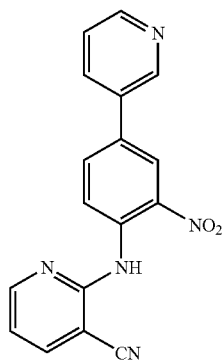

2-(2-nitro-4-(pyridin-3-yl)phenylamino)pyridine-3-carbonitrile To a stirred solution of 0.5 g of 2-nitro-4-(pyridin-3-yl)benzenamine in 3 mL of DMF was added 2.267 g of Cs₂CO₃ followed by 0.386 g of 2-chloro-3-cyano-pyridine. The reaction mixture was heated to 130° C. for 5 h under nitrogen atmosphere. The reaction mixture was then diluted with ethyl acetate and water. The organic layer was separated, washed with water followed by brine, dried over sodium sulfate, and evaporated to afford a yellow solid (0.440 g, 60%). mp: 91-92° C.

7

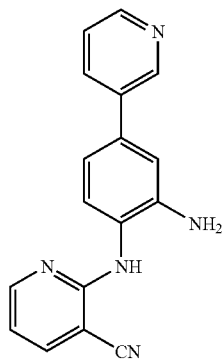

2-(2-amino-4-(pyridin-3-yl)phenylamino)pyridine-3-carbonitrile To the stirred solution of 0.3 g of 2-(2-nitro-4-(pyridin-3-yl)phenylamino)pyridine-3-carbonitrile in 15 mL of ethanol was added 0.471 of stannous chloride at rt. The reaction mixture was refluxed for 2.5 h. The reaction mass was diluted with 20 mL of ethylacetate, 15 mL of water and then made alkaline to pH-8-9 using saturated sodium bicarbonate solution. The organic layer was separated and washed with water followed by brine solution, dried over sodium sulfate and evaporated to afford a yellow solid (0.217 g, 80%). mp: 67-68° C.;

8

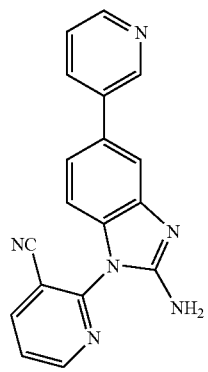

2-(2-amino-5-(pyridin-3-yl)-1H-benzo[d]imidazol-1-yl) pyridine-3-carbonitrile (Compound 18) To a stirred solution of 170 mg of 2-(2-amino-4-(pyridin-3-yl)phenylamino) pyridine-3-carbonitrile in 5 mL of methanol and 5 mL of water was added 65 mg of cyanogen bromide at 0° C. The reaction mixture was allowed to attain rt and stirred at this temperature for 3 h under nitrogen atmosphere. The reaction mass was diluted with 20 mL of ethylacetate, 15 mL of water, then made alkaline to pH-8 using saturated sodium bicarbonate solution. The organic layer was separated and washed with water followed by brine solution, dried over sodium sulfate, and evaporated to afford a crude solid. The crude compound was purified on preparative TLC using 5% MeOH/CHCl₃ as eluent to form a pale yellow solid (25 mg, 10.6%). LC/MS 313.2 [M+H] ¹HNMR (300 MHz, CDCl₃): 8.99 (br.d, J=3.0 Hz, 1H), 8.83 (dd, J=8.1 Hz, 1H), 8.73 (d, J=8.4 Hz, 1H), 8.57 (dd, J=3.3 Hz, 1H), 8.24 (br.s, 1H), 8.18 (dt, J=2.1 Hz, 1H), 7.96 (d, 1H, J=1.5 Hz), 7.65 (m, 3H), 7.51 (q, 2H, J=4.8 Hz).

Compounds 16-18 were made in a manner similar to Example 2.

Table 2 below depicts data for certain examplary compounds. Compound numbers correspond to those compounds depicted in Table 1.

The following analytical methods were used.

Method A

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture, column gradient conditions are 5%-100% acetonitrile-methanol over 4.5 mins gradient time and 6.2 mins run time on an ACE C8 3.0×75 mm column. Flow rate is 1.0 ml/min.

Method B

Mass spec. samples were analyzed on a MicroMass ZQ, ZMD or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with either 0.2% formic acid or 0.1% TFA as a modifier. Column gradient conditions are 10%-90% acetonitrile over 3 mins gradient time and 5 mins run time on a Waters YMC Pro-C18 4.6×50 mm column. Flow rate is 1.5 ml/min.

Method C

Same as Method C except that the column gradient conditions are 5%-45% acetonitrile over 5 mins gradient time and 7 mins run time on a Waters YMC Pro-C18 2×50 mm column. Flow rate is 1.0 ml/min.

TABLE 2

| No | M + 1 (obs) | 1H NMR | Rt (mins) | Mass Spec method |
|---|---|---|---|---|
| 1 | 312.5 | $^1$H NMR(DMSO-$d_6$): 0.94(6H, s), 1.95(1H, m), 2.86(1H, br s), 3.13(1H, br s), 4.34(1H, m), 6.92(1H, s), 7.28(1H, t), 7.32(1H, t), 7.45(1H, d), 7.55(1H, d), 7.93(4H, m), 8.56(1H, s), 8.83(2H, br s) | 6.796 | A |
| 2 | 340.45 | $^1$H NMR(DMSO-$d_6$): 0.94(6H, m), 1.95(1H, m), 2.31(6H, s), 2.87(1H, m), 3.11(1H, m), 4.34(1H, s), 6.90(1H, s), 7.25(1H, s), 7.36(1H, s), 7.94(4H, m), 8.55(1H, s), 8.84(2H, s) | 7.939 | A |
| 3 | 310.49 | $^1$H NMR(DMSO-$d_6$): 1.58(1H, m), 1.75(1H, m), 1.92(2H, m), 2.88(2H, m), 3.16(1H, m), 3.38(1H, m), 4.33(1H, br s), 6.93(1H, s), 7.27(1H, t), 7.31(1H, t), 7.49(1H, d), 7.54(1H, d), 8.46(1H, m), 8.61(1H, s), 9.11(2H, s), 9.24(1H, s), 9.35(1H, s) | 5.874 | A |
| 4 | 338.43 | $^1$H NMR(DMSO-$d_6$): 1.62(1H, m), 1.74(1H, m), 1.94(1H, d), 2.03(1H, d), 2.30(6H, d), 2.84(2H, m), 3.22(1H, d), 3.42(1H, d), 4.27(1H, br s), 6.85(1H, s), 7.25(1H, s), 7.34(1H, s), 8.22(1H, d), 8.60(1H, s), 8.85(1H, s), 8.97(3H, m) | 7.134 | A |
| 5 | 297 | $^1$H NMR(CD$_3$SOCD$_3$, 400 MHz): d 0.91(d, 6H), 2.03-2.14(m, 1H), 3.02-3.67(m, 5H), 6.84-7.11(m, 1H), 7.25-7.39(m, 2H), 7.47(d, 1H), 7.52-7.66(m, 1H), 8.61(s, 1H), 8.91(s, br., 2H) | 2.00 | B |
| 6 | 410.5 | $^1$H NMR(DMSO-$d_6$): 1.48(9H, s), 1.76(5H, m), 2.01(1H, m), 3.60(3H, m), 5.36(1H, br s), 6.37(2H, s), 6.66(1H, s), 7.13(1H, t), 7.22(1H, t), 7.44(2H, d), 8.58(1H, s) | 9.263 | A |
| 7 | 412.58 | $^1$H NMR(DMSO-$d_6$): 1.58(1H, m), 1.75(1H, m), 1.92(2H, m), 2.88(2H, m), 3.16(1H, m), 3.38(1H, m), 4.33(1H, br s), 6.93(1H, s), 7.27(1H, t), 7.31(1H, t), 7.49(1H, d), 7.54(1H, d), 8.46(1H, m), 8.61(1H, s), 9.11(2H, s), 9.24(1H, s), 9.35(1H, s) | 9.295 | A |
| 8 | 352.1 | $^1$H NMR(CD$_3$SOCD$_3$, 400 MHz): d 1.75-1.81(m, 1H), 1.83-1.89(m, 1H), 1.97(s, 3H), 3.40-3.56(m, 2H), 3.62-3.80(m, 4H), 3.87-4.08(m, 2H), 7.05-7.18(m, 1H), 7.27-7.32(m, 1H), 7.33-7.38(m, 1H), 7.46-7.59(m, 2H), 8.65(d, 1H), 8.96(s, br., 2H) | 2.10 | C |
| 9 | 294.9 | $^1$H NMR(CD$_3$SOCD$_3$, 400 MHz): d 1.14-1.29(m, 3H), 1.70-1.79(m, 1H), 1.94-2.17(m, 4H), 3.27-3.74(m, 2H), 6.72-6.90(m, 1H), 7.26-7.63(m, 4H), 8.61(s, 1H), 8.92(s, br., 2H) | 1.80 | B |
| 10 | 309 | 1H NMR(CD$_3$SOCD$_3$, 400 MHz): d 1.48-1.58(m, 4H), 1.71-1.79(m, 4H), 3.53-3.61(m, 2H), 3.84-3.90(m, 2H), 6.96(s, 1H), 7.26-7.37(m, 2H), 7.46(d, 1H), 7.50(d, 1H), 8.61(s, 1H), 8.85(s, br., 2H) | 2.00 | B |
| 11 | 335 | $^1$H NMR(CD$_3$SOCD$_3$, 400 MHz): d 1.61-1.68(m, 8H), 2.12-2.19(m, 2H), 3.52-4.41(m, 4H), 7.17(s, 1H), 7.27-7.38(m, 2H), 7.44-7.52(m, 2H), 8.61(s, 1H), 8.85(s, br., 2H) | 2.30 | B |
| 12 | 346.9 | $^1$H NMR(CD$_3$SOCD$_3$, 400 MHz): d 3.67-3.76(m, 2H), 5.22-5.30(m, 1H), 6.99-7.61(m, 10H), 8.38-8.68(m, 2H), 9.00(s, br., 2H) | 1.80 | B |
| 13 | 324.9 | $^1$H NMR(CD$_3$SOCD$_3$, 400 MHz): d 1.56-2.02(m, 8H), 3.69(s, 2H), 6.91(s, 1H), 7.28-7.74(m, 5H), 8.52(s, 1H), 8.99(s, br., 2H) | 1.80 | B |
| 14 | 320.9 | $^1$H NMR(CD$_3$SOCD$_3$, 400 MHz): d 7.16-7.64(m, 8H), 7.95-8.02(m, 1H), 8.72(s, 1H), 8.85(s, br., 2H), 9.89(s, 1H) | 2.00 | B |
| 15 | 366.1 | $^1$H NMR(CD$_3$SOCD$_3$, 400 MHz): d 1.08-1.27(m, 6H), 2.07(s, 3H), 3.17-3.32(m, 2H), 4.00-4.75(m, 4H), 7.23-7.49(m, 5H), 8.65(s, 1H), 8.85(s, br., 2H) | 1.60 | B |
| 16 | — | $^1$H NMR(CDCl$_3$) :d 8.92(d, 1H), 8.83(s, 1H), 8.81(s, 1H), 8.57(dd, 1H), 8.51(d, 1H), 7.92(dt, 1H), 7.6(s, 1H), 7.32-7.38(m, 2H), 7.21(m, 2H), 7.10(bs, 1H). | — | — |
| 17 | — | $^1$H NMR(CDCl$_3$, 300 MHz): 8.9(s, 1H), 8.6(br. t, J = 7.5 Hz, 2H), 7.9(m, 2H), 7.72(d, J = 8.4 Hz, 1H), 7.66(s, 1H), 7.52(d, J = 8.4 Hz, 1H), 7.28(m, 3H), 6.4(bs, 2H). | — | — |
| 18 | — | $^1$H NMR(CDCl$_3$, 300 MHz): 8.99(br. d, J = 3.0 Hz, 1H), 8.83(dd, J = 8.1 Hz, 1H), 8.73(d, J = 8.4 Hz, 1H), 8.57(dd, J = 3.3 Hz, 1H), 8.24(br.s, 1H), 8.18(dt, J = 2.1 Hz, 1H), 7.96(d, 1H, J = 1.5 Hz), 7.65(m, 3H), 7.51(q, 2H, J = 4.8 Hz). | — | — |
| 19 | 246.26 | $^1$H NMR(DMSO-$d_6$): 7.01(1H, t), 7.14(1H, t), 7.18(2H, s), 7.27(1H, d), 7.63(1H, d), 7.97(1H, s), 9.08(1H, s); 1H NMR(CD$_3$SOCD$_3$, 400 MHz): d 7.23-7.28(m, 1H), 7.32-7.36(m, 1H), 7.45(d, 1H), 7.66(d, 1H), 8.13(s, 1H), 8.81(s, br., 2H), 9.22(s, 1H) | 7.778 | A |

TABLE 2-continued

| No | M + 1 (obs) | 1H NMR | Rt (mins) | Mass Spec method |
|---|---|---|---|---|
| 20 | 294.90 | $^1$H NMR(CD$_3$SOCD$_3$, 400 MHz): d 1.14-1.29(m, 3H), 1.70-1.79(m, 1H), 1.94-2.17(m, 4H), 3.27-3.74(m, 2H), 6.72-6.90(m, 1H), 7.26-7.63(m, 4H), 8.61(s, 1H), 8.92(s, br., 2H) | 1.80 | B |
| 21 | 366.10 | $^1$H NMR(CD$_3$SOCD$_3$, 400 MHz): d 1.08-1.27(m, 6H), 2.07(s, 3H), 3.17-3.32(m, 2H), 4.00-4.75(m, 4H), 7.23-7.49(m, 5H), 8.65(s, 1H), 8.85(s, br., 2H) | 1.60 | B |
| 22 | 283.29 | $^1$H NMR(DMSO-d$_6$): 2.28(6H, d), 3.16(6H, s), 6.71(1H, s), 6.95(2H, s), 7.03(1H, s), 7.31(1H, s), 8.53(1H, s) | 8.862 | A |
| 23 | 269.31 | $^1$H NMR(DMSO-d$_6$): 2.24(6H, d), 2.90(3H, s), 6.57(1H, s), 7.02(3H, s), 7.20(1H, s), 7.72(1H, m), 8.48(1H, s) | 8.862 | A |
| 24 | 311.32 | $^1$H NMR(DMSO): 0.95(6H, d), 1.88(1H, m), 2.24(6H, d), 3.23(2H, m), 6.78(1H, s), 7.03(1H, s), 7.08(2H, s), 7.25(1H, s), 7.80(1H, t), 8.44(1H, s) | 9.69 | A |
| 25 | 352.36 | $^1$H NMR(DMSO): 1.26(2H, m), 1.53(1H, m), 1.84(2H, m), 2.29(1H, m), 2.31(6H, d), 2.67(3H, m), 3.27(2H, t), 6.84(1H, s), 7.26(1H, s), 7.36(1H, s), 8.21(1H, t), 8.56(1H, s), 8.75(1H, d), 8.97(2H, s) | 7.235 | A |
| 26 | 338.37 | $^1$H NMR(DMSO): 1.81(1H, m), 2.08(1H, m), 2.31(6H, d), 2.59(1H, m), 2.98(1H, m), 3.37(4H, m), 3.50(1H, t), 6.83(1H, s), 7.35(1H, s), 8.02(1H, s), 8.24(1H, t), 8.57(1H, s), 8.81(2H, br s), 8.95(1H, s) | 9.984 | A |
| 27 | 365.44 | $^1$H NMR(CDCl$_3$): 1.19(3H, m), 1.23(6H, m), 1.55(1H, br s), 1.80(6H, m), 2.34(5H, m), 5.70(1H, br s), 6.58(1H, s), 6.60(1H, br s), 7.22(2H, s), 7.73(1H, s), 8.46(1H, s), 8.92(1H, s) | 10.888 | A |
| 28 | 389.42 | $^1$H NMR(CDCl$_3$): 2.14(3H, m), 2.21(6H, m), 3.83(2H, m), 6.77(1H, br s), 7.08(1H, s), 7.38(3H, m), 7.43(4H, m), 8.43(1H, s) | 9.016 | A |
| 29 | 341.38 | $^1$H NMR(CDCl$_3$): 1.07(6H, d), 2.06(2H, m), 2.20(6H, m), 3.85(1H, m), 3.92(1H, m), 6.00(1H, d), 6.37(1H, s), 6.70(1H, br s), 7.01(1H, s), 7.16(1H, s), 8.35(1H, s) | 8.801 | A |
| 30 | 359.35 | $^1$H NMR(CDCl$_3$): 1.65(3H, d), 2.12(3H, s), 2.28(3H, s), 4.72(1H, br s), 6.39(2H, br s), 6.94(2H, br s), 7.14(1H, s), 7.40(5H, m), 8.49(1H, s) | 9.872 | A |
| 31 | 324.32 | $^1$H NMR(DMSO-d$_6$): 2.15(1H, br s), 2.31(6H, d), 2.38(1H, br s), 3.75(5H, br m), 6.86(1H, s), 7.26(1H, s), 7.35(1H, s), 8.25(3H, d), 8.66(1H, s), 8.91(2H, s) | 7.189 | A |
| 32 | 324.32 | $^1$H NMR(DMSO-d$_6$): 2.18(1H, br s), 2.31(6H, d), 2.46(1H, s), 3.84(5H, br m), 6.86(1H, s), 7.27(1H, s), 7.35(1H, s), 8.27(2H, s), 8.66(1H, s), 8.94(2H, s) | 7.200 | A |
| 33 | 338.37 | $^1$H NMR(DMSO-d$_6$): 1.64(4H, m), 1.85(1H, m), 2.08(1H, m), 2.31(6H, d), 3.23(3H, m), 7.16(1H, s), 7.26(1H, s), 7.31(1H, s), 8.08(3H, s), 8.67(1H, s), 8.89(2H, s) | 7.572 | A |
| 34 | 338.37 | $^1$H NMR(DMSO-d$_6$): 1.67(4H, m), 1.85(1H, m), 2.07(1H, m), 2.31(6H, d), 3.23(3H, m), 7.16(1H, s), 7.26(1H, s), 7.31(1H, s), 8.10(3H, s), 8.67(1H, s), 8.90(2H, s) | 7.550 | A |
| 35 | 331.32 | $^1$H NMR(CDCl$_3$): 2.35(6H, d), 7.27(4H, m), 7.44(2H, t), 7.64(1H, d), 7.76(1H, s), 8.95(1H, s) | 9.768 | A |
| 36 | 298.31 | $^1$H NMR(DMSO-d$_6$): 2.33(6H, d), 3.04(2H, d), 3.66(2H, d), 6.86(1H, s), 7.25(1H, s), 7.33(1H, s), 7.92(3H, br s), 8.22(1H, s), 8.60(1H, s), 8.87(2H, s) | 6.640 | A |
| 37 | 352.43 | $^1$H NMR(DMSO-d$_6$): 1.24(4H, m), 1.91(4H, m), 2.29(6H, d), 2.51(1H, br s), 3.89(1H, br s), 6.73(1H, s), 7.12(1H, s), 7.30(1H, s), 8.02(3H, br s), 8.16(1H, d), 8.55(1H, d), 8.83(2H, s) | 7.514 | A |
| 38 | 374.39 | $^1$H NMR(DMSO-d$_6$): 2.33(6H, d), 4.05(2H, d), 4.69(2H, d), 6.92(1H, s), 7.13(1H, s), 7.40(5H, m), 8.19(3H, br s), 8.56(2H, m), 8.89(2H, s) | 7.799 | A |
| 39 | 312.29 | $^1$H NMR(MeOD): 2.04(2H, m), 2.35(6H, d), 3.07(2H, t), 3.66(2H, m), 6.88(1H, s), 7.19(1H, s), 7.37(1H, s), 8.56(1H, s) | 6.816 | A |
| 40 | 361.38 | $^1$H NMR(DMSO-d$_6$): 2.31(6H, d), 3.87(3H, s), 7.02(1H, m), 7.18(3H, m), 7.37(1H, s), 7.44(1H, s), 7.84(1H, s), 8.67(1H, s), 8.88(2H, s), 9.50(1H, s) | 9.739 | A |
| 41 | 361.31 | $^1$H NMR(DMSO-d$_6$): 2.31(6H, d), 3.78(3H, s), 6.71(1H, d), 7.23(2H, s), 7.28(1H, m), 7.42(2H, s), 8.78(3H, m), 10.14(1H, s) 13.06(1H, br s) | 9.770 | A |
| 42 | 361.31 | $^1$H NMR(DMSO-d$_6$): 2.31(6H, d), 3.76(3H, s), 6.99(3H, m), 7.23(1H, s), 7.39(1H, s), 7.59(2H, s), 8.81(1H, s), 8.97(2H, s), 9.98(1H, s) | 9.557 | A |
| 43 | 365.30 | $^1$H NMR(DMSO-d$_6$): 2.33(6H, d), 7.15(2H, m), 7.26(1H, s), 7.42(2H, m), 7.58(1H, d), 8.06(1H, s), 8.81(3H, m), 10.32(1H, s) | 10.366 | A |
| 44 | 365.30 | $^1$H NMR(DMSO-d$_6$): 2.47(6H, d), 7.24(1H, s), 7.37(1H, s), 7.60(3H, m), 7.94(2H, d), 8.92(3H, m), 10.58(1H, s) | 10.238 | A |

BIOLOGICAL METHODS

Example 1

Aurora B Inhibition Assay (Radiometric)

An assay buffer solution was prepared which consisted of 25 mM HEPES (pH 7.5), 10 mM MgCl$_2$, 0.1% BSA and 10% glycerol. A 22 nM Aurora-B solution, also containing 1.7 mM DTT and 1.5 mM Kemptide (LRRASLG), was prepared in assay buffer. To 22 μL of the Aurora-B solution, in a 96-well plate, was added 2 μl of a compound stock solution in DMSO and the mixture allowed to equilibrate for 10 minutes at 25° C. The enzyme reaction was initiated by the addition of 16 μl stock [γ-$^{33}$P]-ATP solution (~20 nCi/μL) prepared in assay buffer, to a final assay concentration of 800 μM. The reaction was stopped after 3 hours by the addition of 16 μL 500 mM phosphoric acid and the levels of $^{33}$P incorporation into the peptide substrate were determined by the following method. A phosphocellulose 96-well plate (Millipore, Cat no. MAPH-NOB50) was pre-treated with 100 μL of a 100 mM phosphoric acid prior to the addition of the enzyme reaction mixture (40 μL). The solution was left to soak on to the phosphocellulose membrane for 30 minutes and the plate subsequently washed four times with 200 μL of a 100 mM phosphoric acid. To each well of the dry plate was added 30 μL of Optiphase 'SuperMix' liquid scintillation cocktail (Perkin Elmer) prior to scintillation counting (1450 Microbeta Liquid Scintillation Counter, Wallac). Levels of non-enzyme catalysed background radioactivity were determined by adding 16 μL of the 500 mM phosphoric acid to control wells, containing all assay components (which acts to denature the enzyme), prior to the addition of the [γ-$^{33}$P]-ATP solution. Levels of enzyme catalysed $^{33}$P incorporation were calculated by subtracting mean background counts from those measured at each inhibitor concentration. For each Ki determination 8 data points, typically covering the concentration range 0-10 μM compound, were obtained in duplicate (DMSO stocks were prepared from an initial compound stock of 10 mM with subsequent 1:2.5 serial dilutions). Ki values were calculated from initial rate data by non-linear regression using the Prism software package (Prism 3.0, Graphpad Software, San Diego, Calif.).

The following compounds inhibited Aurora-B with a Ki value of <1 uM: Compounds 1-4, 14, and 28.

Example 2

FLT-3 Inhibition Assay

Compounds were screened for their ability to inhibit FLT-3 activity using a radiometric filter-binding assay. This assay monitors the 33P incorporation into a substrate poly(Glu, Tyr) 4:1 (pE4Y). Reactions were carried out in a solution containing 100 mM HEPES (pH 7.5), 10 mM $MgCl_2$, 25 mM NaCl, 1 mM DTT, 0.01% BSA and 2.5% DMSO. Final substrate concentrations in the assay were 90 μM ATP and 0.5 mg/ml pE4Y (both from Sigma Chemicals, St Louis, Mo.). The final concentration of a compound of the present invention is generally between 0.01 and 5 μM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH 7.5), 10 mM $MgCl_2$, 25 mM NaCl, 1 mg/ml pE4Y and 180 mM ATP (containing 0.3 mCi of [γ-33$^P$]ATP for each reaction). Solution 2 contains 100 mM HEPES (pH 7.5), 10 mM $MgCl_2$, 25 mM NaCl, 2 mM DTT, 0.02% BSA and 3 nM FLT-3. The assay was run on a 96 well plate by mixing 50 μl each of Solution 1 and 2.5 ml of the compounds of the present invention. The reaction was initiated with Solution 2. After incubation for 20 minutes at room temperature, the reaction was stopped with 50 μl of 20% TCA containing 0.4 mM of ATP. All of the reaction volume was then transferred to a filter plate and washed with 5% TCA by a Harvester 9600 from TOMTEC (Hamden, Conn.). The amount of $^{33}$P incorporation into pE4y was analyzed by a Packard Top Count Microplate Scintillation Counter (Meriden, Conn.). The data was fitted using Prism software to get an IC50 or Ki.

The following compounds inhibited FLT-3 with a Ki value of <1 uM: Compounds 1-5, 8-17, 20-42, and 44.

Example 3

PDK-1 Inhibition Assay

Compounds are screened for their ability to inhibit PDK-1 using a radioactive-phosphate incorporation assay (Pitt and Lee, J. Biomol. Screen., (1996) 1, 47). Assays are carried out in a mixture of 100 mM HEPES (pH 7.5), 10 mM $MgCl_2$, 25 mM NaCl, 2 mM DTT. Final substrate concentrations in the assay are 40 μM ATP (Sigma Chemicals) and 65 μM peptide (PDKtide, Upstate, Lake Placid, N.Y.). Assays are carried out at 30° C. and 25 nM PDK-1 in the presence of ~27.5 nCi/μL of [γ-$^{32}$P]ATP (Amersham Pharmacia Biotech, Amersham, UK). An assay stock buffer solution is prepared containing all of the reagents listed above, with the exception of ATP, and the test compound of interest. 15 μl of the stock solution is placed in a 96 well plate followed by addition of 1 μl of 0.5 mM DMSO stock containing the test compound (final compound concentration 25 μM, final DMSO concentration 5%). The plate is preincubated for about 10 minutes at 30° C. and the reaction initiated by addition of 4 μl ATP (final concentration 40 μM).

The reaction is stopped after 10 minutes by the addition of 100 μL 100 mM phosphoric acid, 0.01% Tween-20. A phosphocellulose 96 well plate (Millipore, Cat no. MAPH-NOB50) is pretreated with 100 μL 100 mM phosphoric acid, 0.01% Tween-20 prior to the addition of the reaction mixture (100 μL). The spots are left to soak for at least 5 minutes, prior to wash steps (4×200 μL 100 mM phosphoric acid, 0.01% Tween-20). After drying, 20 μL Optiphase 'SuperMix' liquid scintillation cocktail (Perkin Elmer) is added to the well prior to scintillation counting (1450 Microbeta Liquid Scintillation Counter, Wallac).

Compounds showing greater than 50% inhibition versus standard wells containing the assay mixture and DMSO without test compound are titrated to determine $IC_{50}$ values.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:
1. A compound of formula (I):

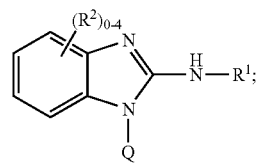

or a pharmaceutically acceptable salt thereof;
wherein
Q is selected from the group consisting of

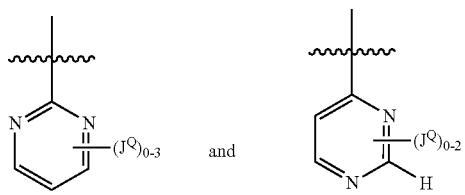

$R^1$ is H, $C_{1-6}$aliphatic, or $C_{3-8}$cycloaliphatic optionally substituted with 0-4 $J^R$;
each $R^2$ is independently $Z^R$, $M^R$, $(L^R)$-$Z^R$ or $(X^R)$-$M^R$;
each $J^Q$ is independently $Z^Q$, $M^Q$, $(L^Q)$-$Z^Q$, or $(X^Q)$-$M^Q$;

each $L^R$, $L^Q$, $X^R$, and $X^Q$ is independently $C_{1-6}$alkyl optionally interrupted with up to 2 occurrences of —NR—, —O—, —S—, —CO$_2$—, —OC(O)—, —C(O)CO—, —C(O)—, —C(O)NR—, —C(=N—CN), —C(=N—OH), —NRCO—, —NRC(O)O—, —SO$_2$NR—, —NRSO$_2$—, —NRC(O)NR—, —OC(O)NR—, —NRSO$_2$NR—, —SO—, or —SO$_2$—;
wherein
    each $L^R$ is independently and optionally substituted with 0-2 $J^{LR}$;
    each $L^Q$ is independently and optionally substituted with 0-2 $J^{LQ}$;
    each $X^R$ is independently and optionally substituted with 0-2 $J^{XR}$;
    each $X^Q$ is independently and optionally substituted with 0-2 $J^{XQ}$;
each $Z^R$ and $Z^Q$ is independently H; $C_{1-6}$ aliphatic; a 3-8-membered saturated, partially unsaturated, or fully unsaturated monocyclic ring having 0-3 heteroatoms independently selected from nitrogen, oxygen, and sulfur; or an 8-12 membered saturated, partially unsaturated, or fully unsaturated bicyclic ring system having 0-5 heteroatoms independently selected from nitrogen, oxygen, and sulfur; wherein
    each $Z^R$ is independently and optionally substituted with 0-4 $J^{ZR}$;
    each $Z^Q$ is independently and optionally substituted with 0-4 $J^{ZQ}$;
$M^Q$ is independently CN, CF$_3$, NO$_2$, OR, SR, or N(R)$_2$;
$M^R$ is independently halo, CN, CF$_3$, NO$_2$, OR, SR, or N(R)$_2$;
each $J^R$ is independently $C_{1-6}$aliphatic, $C_{1-6}$haloalkyl, halo, OH, $C_{1-3}$alkoxy, NO$_2$, or CN;
each $J^{LR}$, $J^{LQ}$, $J^{XR}$, $J^{XQ}$, $J^{ZR}$, and $J^{ZQ}$ is independently V, M, (L$^V$)-V, (L$^M$)-M, $C_{1-6}$haloalkyl, halo, OH, $C_{1-3}$alkoxy, NO$_2$, or CN;
each R is independently H, $C_{1-6}$aliphatic, $C_{6-10}$aryl, —($C_{1-6}$aliphatic)-($C_{6-10}$aryl), $C_{3-8}$cycloaliphatic, —C(=O)($C_{1-6}$aliphatic), —C(=O)($C_{3-8}$cycloaliphatic), or —C(=O)O($C_{1-6}$aliphatic); wherein each R is independently and optionally substituted with 0-2 J;
each L$^V$ and L$^M$ is independently $C_{1-6}$alkyl optionally interrupted with up to 2 occurrences of —NR—, —O—, —S—, —CO$_2$—, —OC(O)—, —C(O)CO—, —C(O)—, —C(O)NR—, —C(=N—CN), —C(=N—OH), —NRCO—, —NRC(O)O—, —SO$_2$NR—, —NRSO$_2$—, —NRC(O)NR—, —OC(O)NR—, —NRSO$_2$NR—, —SO—, or —SO$_2$—;
wherein
    each L$^V$ is independently and optionally substituted with 0-2 $J^{LV}$;
    each L$^M$ is independently and optionally substituted with 0-2 $J^{LM}$;
each V is independently H; $C_{1-6}$ aliphatic; a 3-8-membered saturated, partially unsaturated, or fully unsaturated monocyclic ring having 0-3 heteroatoms independently selected from nitrogen, oxygen, and sulfur; or an 8-12 membered saturated, partially unsaturated, or fully unsaturated bicyclic ring system having 0-5 heteroatoms independently selected from nitrogen, oxygen, and sulfur; wherein each V is independently and optionally substituted with 0-2 $J^V$;
each J, $J^{LV}$, $J^{LM}$, and $J^V$ is independently R', $C_{3-6}$cycloalkyl, $C_{1-6}$haloalkyl, halo, NO$_2$, CN, OH, OR', SH, SR', NH$_2$, NHR', N(R')$_2$, COH, COR', CONH$_2$, CONHR', CON(R')$_2$, NHCOR', NR'COR', NHCONH$_2$, NHCONHR', NHCON(R')$_2$, NR'CONH$_2$, NR'CONHR', NR'CON(R')$_2$, SO$_2$NH$_2$, SO$_2$NHR', SO$_2$N(R')$_2$, NHSO$_2$R', or NR'SO$_2$R';
R' is unsubstituted $C_{1-6}$aliphatic; or two R' groups, together with the atom to which they are bound, form an unsubstituted 3-8 membered saturated or partially saturated monocyclic ring having 0-1 heteroatoms independently selected from nitrogen, oxygen, and sulfur;
each M is independently halo, CN, CF$_3$, NO$_2$, OH, O($C_{1-6}$alkyl), SH, S($C_{1-6}$alkyl), NH$_2$, NH($C_{1-6}$alkyl), or N($C_{1-6}$alkyl)$_2$;
provided that
    when Q is

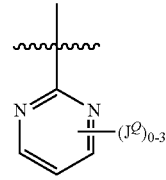

and R$^2$ is H, F, Cl, CH$_3$, CF$_3$, OCH$_3$, or OCH$_2$CH$_3$ at the 5 or 6 position of the benzimidazole ring, then $J^Q$ is not —O—($C_{1-3}$aliphatic);
when Q is

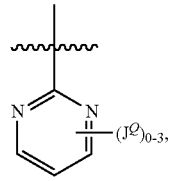

then $J^Q$ is not

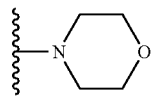

optionally substituted with methyl.

2. The compound of claim 1 wherein R$^1$ is H.
3. The compound of claim 1 wherein Q is

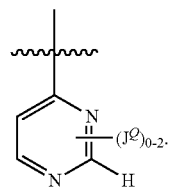

4. The compound of claim 1, wherein $J^Q$ is (L$^Q$)-Z$^Q$ or (X$^Q$)-M$^Q$.
5. The compound of claim 4, wherein L$^Q$ is $C_{1-6}$alkyl optionally interrupted with up to 2 occurrences of —NR—, —O—, —S—, —C(O)—, —C(O)NR—, —NRCO—, —SO$_2$NR—, or —NRSO$_2$—.
6. The compound of claim 5, wherein L$^Q$ is $C_{1-6}$alkyl optionally interrupted with up to 1 occurrence of —NR—.

7. The compound of claim 6, wherein the 1 occurrence of —NR— is attached directly to ring Q.

8. The compound of claim 1, wherein $J^Q$ is $Z^Q$ or $M^Q$.

9. The compound of any one of claims 4-8, wherein $Z^Q$ is H or an optionally substituted group selected from $C_{1-6}$ aliphatic, $C_{3-8}$ cycloaliphatic, phenyl, 5-8 membered heteroaryl, and 5-8 membered heterocyclyl.

10. The compound of claim 4, wherein $X^Q$ is $C_{1-6}$alkyl optionally interrupted with up to 2 occurrences of —NR—, —O—, —S—, —C(O)—, —C(O)NR—, —NRCO—, —SO$_2$NR—, or —NRSO$_2$—.

11. The compound of claim 10, wherein $X^Q$ is $C_{1-6}$alkyl optionally interrupted with up to 1 occurrence of —NR—.

12. The compound of claim 4, wherein ring Q is substituted with 2 occurrences of $J^Q$ wherein one $J^Q$ is $(L^Q)$-$Z^Q$ or $(X^Q)$-$M^Q$ and the other $J^Q$ is $Z^Q$ or $M^Q$.

13. The compound of claim 1, wherein each $R^2$ is selected from $Z^R$ or $M^R$.

14. The compound of claim 1, substituted as shown in Formula III:

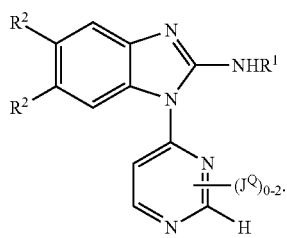

Formula III

15. The compound of claim 14, wherein at least one of $R^2$ is not H.

16. The compound of claim 1 selected from the following:

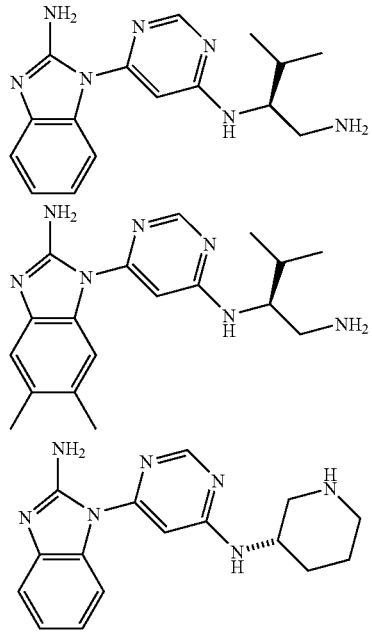

-continued

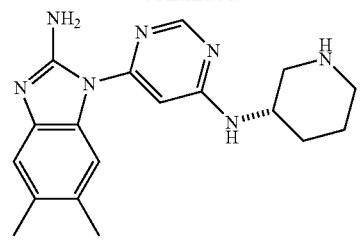

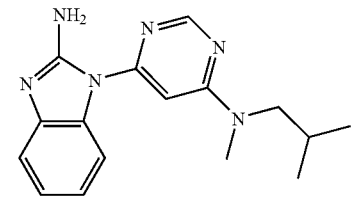

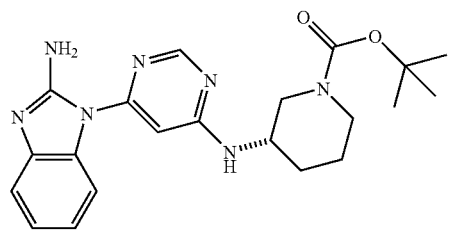

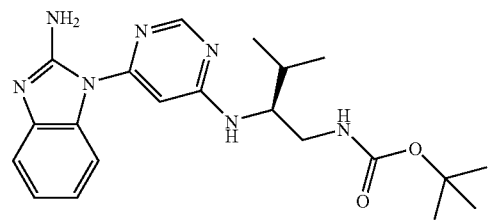

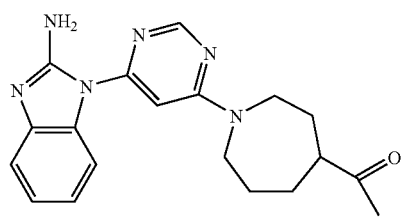

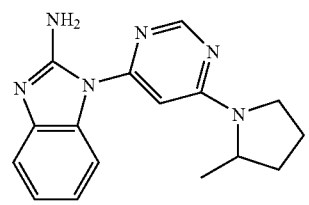

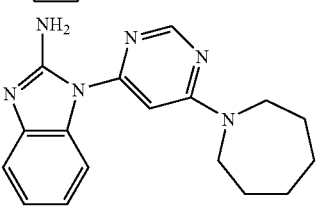

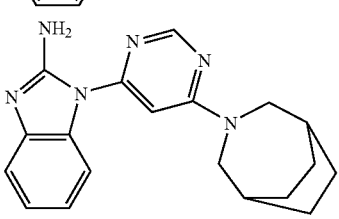

-continued
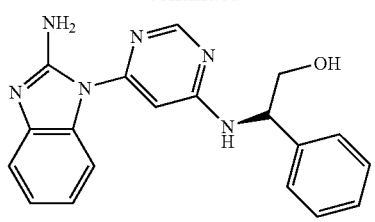
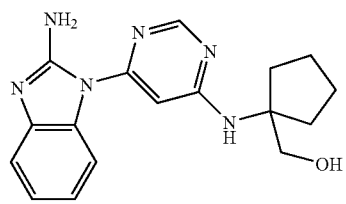
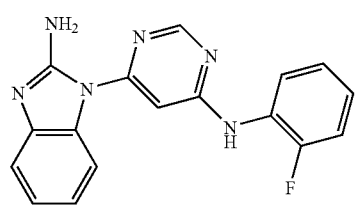
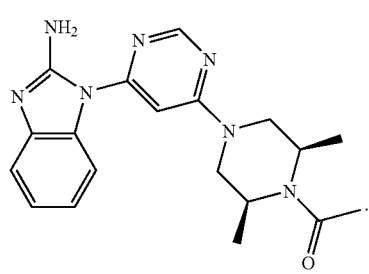
17. The compound of claim 1, selected from the following:
16
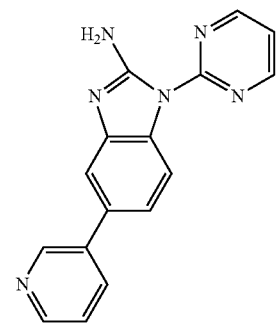
19
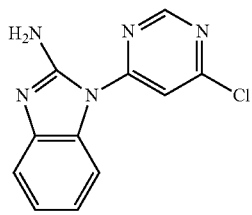
-continued
20
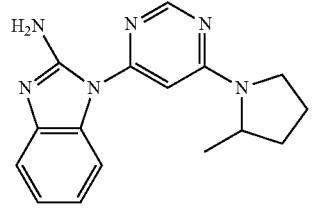
21
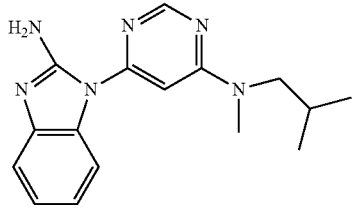
22
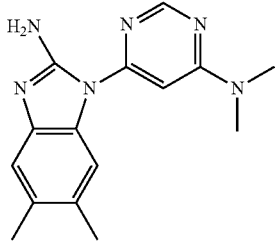
23
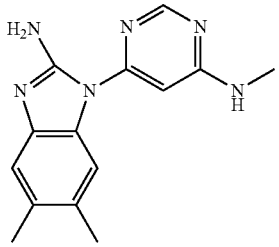
24
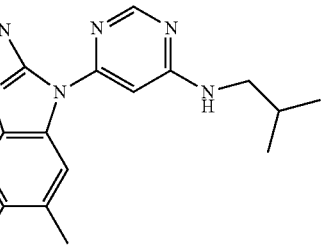
25
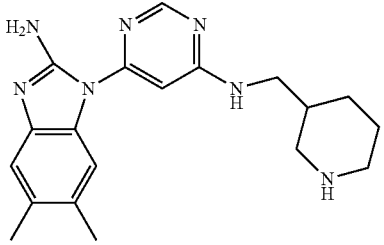

26
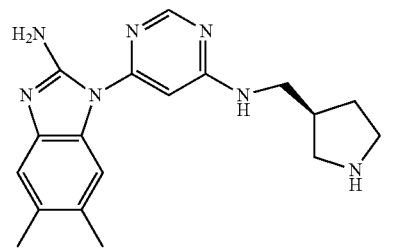
27
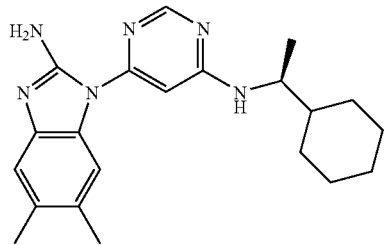
28
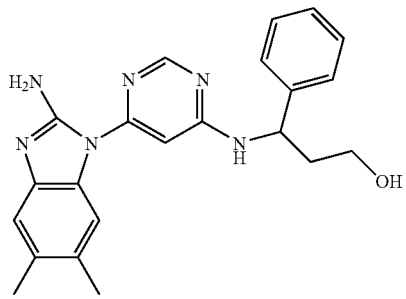
29
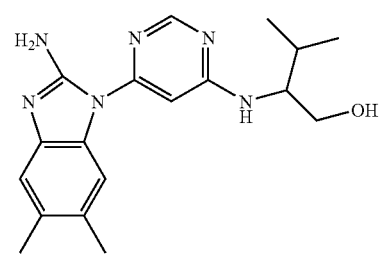
30
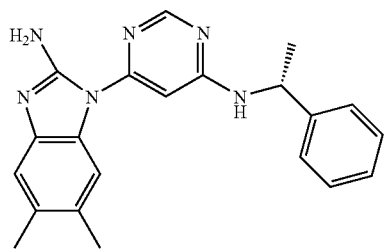
31
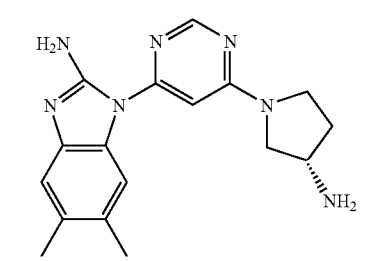
32
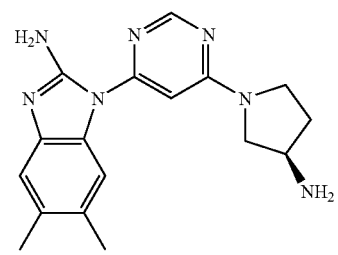
33
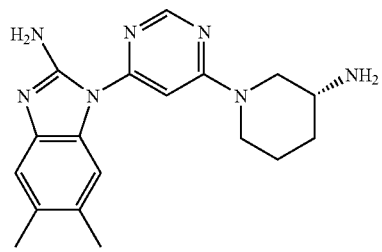
34
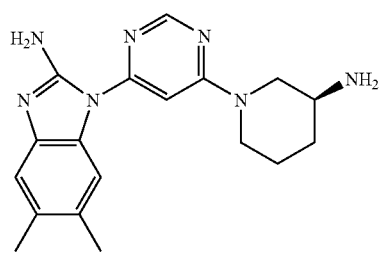
35
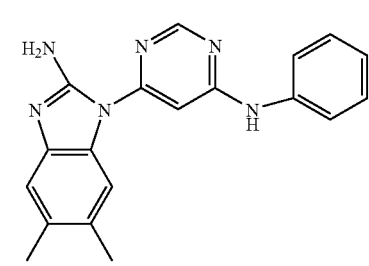
36
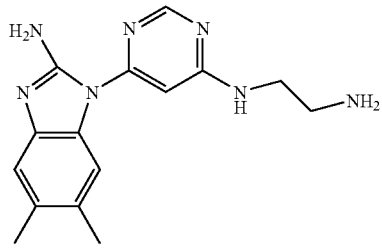
37
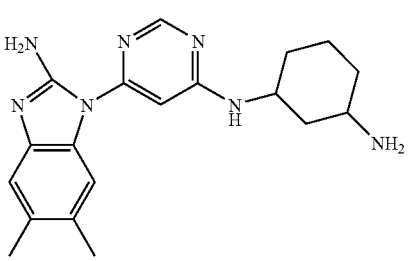

38
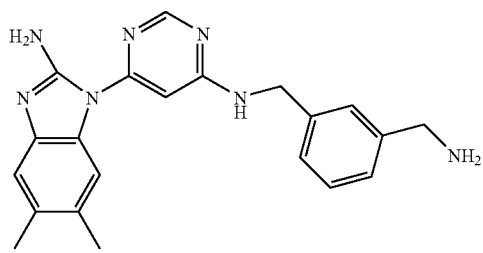
39
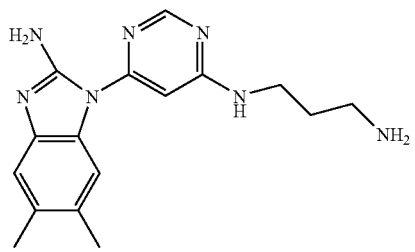
40
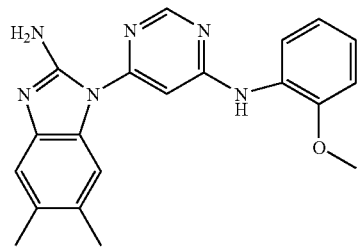
41
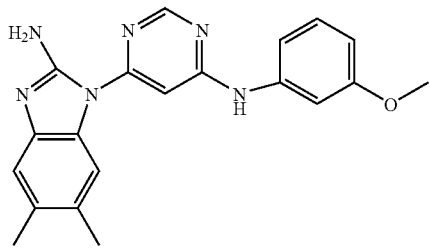
42
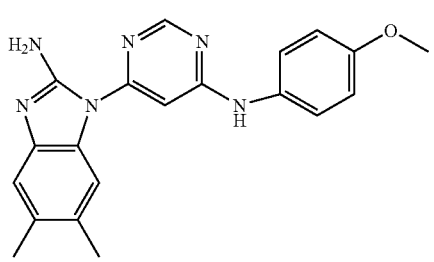
43
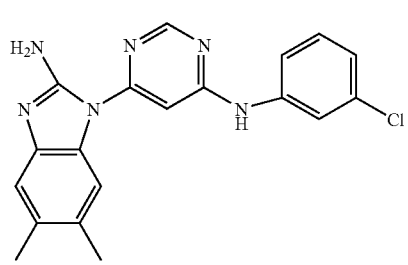
44
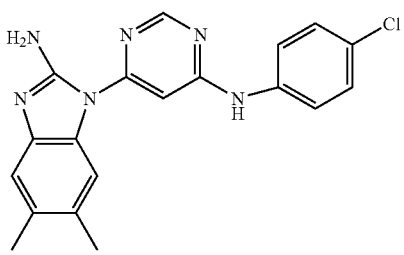
45
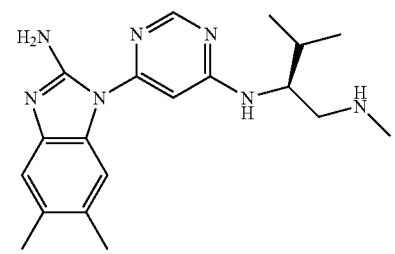
46
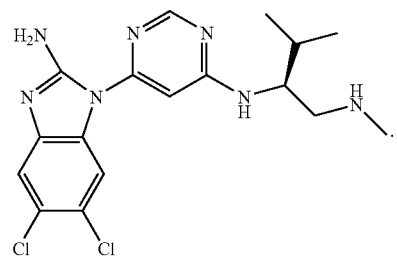
47
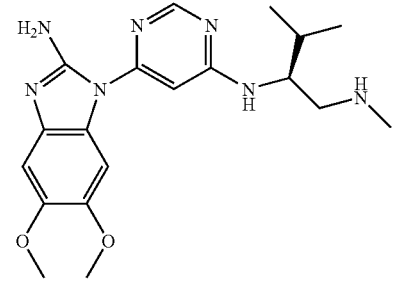
48
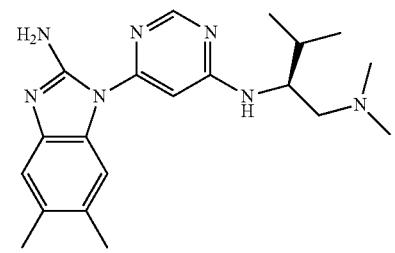
49

61

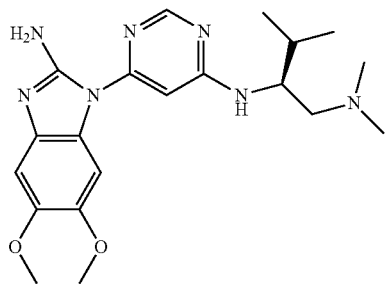

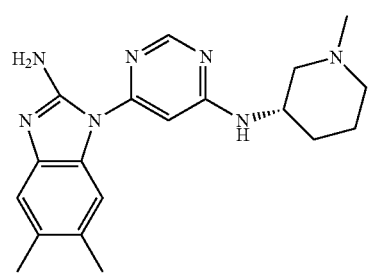

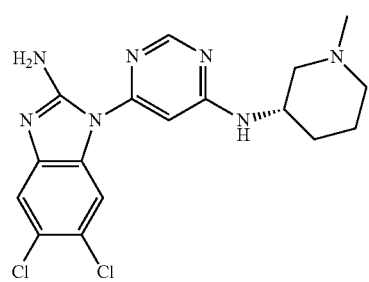

62

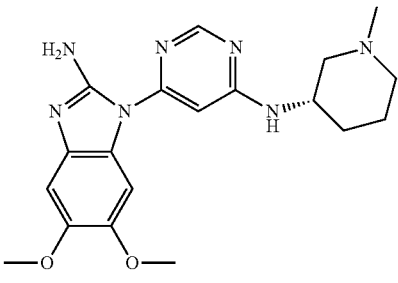

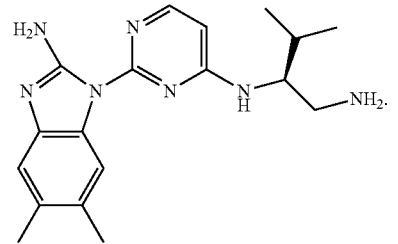

18. A composition comprising a compound of claim 1 and a pharmaceutically acceptable carrier, adjuvant, or vehicle.

19. The compound of claim 14 wherein $R^1$ is H.

20. The compound of claim 14 wherein
 $J^Q$ is $(L^Q)$-$Z^Q$;
 $L^Q$ is $C_{1-6}$alkyl interrupted with 1 occurrence of —NR— attached directly to ring Q; and
 $Z^Q$ is H or an optionally substituted group selected from $C_{1-6}$ aliphatic, $C_{3-8}$ cycloaliphatic, phenyl, 5-8 membered heteroaryl, and 5-8 membered heterocyclyl.

* * * * *